United States Patent
Baell et al.

(10) Patent No.: US 10,954,231 B2
(45) Date of Patent: Mar. 23, 2021

(54) ANXIOLYTIC COMPOUNDS

(71) Applicant: Bionomics Limited, Thebarton (AU)

(72) Inventors: Jonathan Bayldon Baell, Ivanhoe (AU); Brad Sleebs, Reservoir (AU); Bernard Luke Flynn, Donvale (AU); Ian Phillip Street, Macleod (AU); Nurul Quazi, Doncaster (AU); Chinh Thien Bui, North Balwyn (AU)

(73) Assignee: Bionomics Limited, Thebarton (AU)

( * ) Notice: Subject to any disclaimer, the term of this patent is extended or adjusted under 35 U.S.C. 154(b) by 0 days.

(21) Appl. No.: 15/844,264

(22) Filed: Dec. 15, 2017

(65) Prior Publication Data

US 2018/0105523 A1    Apr. 19, 2018

Related U.S. Application Data

(63) Continuation-in-part of application No. 15/398,472, filed on Jan. 4, 2017, now Pat. No. 9,975,892, which is a continuation of application No. 14/533,808, filed on Nov. 5, 2014, now Pat. No. 9,573,945, which is a continuation of application No. 14/030,808, filed on Sep. 18, 2013, now Pat. No. 8,906,912, which is a continuation of application No. 13/617,153, filed on Sep. 14, 2012, now Pat. No. 8,551,990, which is a continuation of application No. 12/311,872, filed as application No. PCT/AU2007/001566 on Oct. 16, 2007, now Pat. No. 8,293,737.

(60) Provisional application No. 60/851,983, filed on Oct. 16, 2006.

(51) Int. Cl.
| | |
|---|---|
| A61K 31/5377 | (2006.01) |
| A61K 31/497 | (2006.01) |
| A61K 31/4375 | (2006.01) |
| C07D 471/04 | (2006.01) |
| A61K 45/06 | (2006.01) |
| A61K 31/519 | (2006.01) |
| A61K 31/4985 | (2006.01) |
| A61K 31/5025 | (2006.01) |

(52) U.S. Cl.
CPC ........ *C07D 471/04* (2013.01); *A61K 31/4375* (2013.01); *A61K 31/497* (2013.01); *A61K 31/4985* (2013.01); *A61K 31/5025* (2013.01); *A61K 31/519* (2013.01); *A61K 31/5377* (2013.01); *A61K 45/06* (2013.01)

(58) Field of Classification Search
CPC .............. A61K 31/4375; A61K 31/497; A61K 31/5377
See application file for complete search history.

(56) References Cited

U.S. PATENT DOCUMENTS

| | | |
|---|---|---|
| 3,429,887 A | 2/1969 | Lesher et al. |
| 4,226,864 A | 10/1980 | Narisada et al. |
| 4,404,201 A | 9/1983 | Haskell et al. |
| 5,095,015 A | 3/1992 | Albaugh |
| 5,182,290 A | 1/1993 | Albaugh |
| 5,182,386 A | 1/1993 | Albaugh et al. |
| 5,212,310 A | 5/1993 | Thurkauf et al. |
| 5,306,819 A | 4/1994 | Albaugh et al. |
| 5,312,822 A | 5/1994 | Albaugh |
| 5,328,912 A | 7/1994 | Albaugh |
| 5,451,585 A | 9/1995 | Albaugh |
| 5,473,073 A | 12/1995 | Albaugh et al. |
| 5,484,944 A | 1/1996 | Albaugh et al. |
| 5,510,480 A | 4/1996 | Albaugh |
| 5,608,079 A | 3/1997 | Albaugh et al. |
| 5,625,063 A | 4/1997 | Thurkauf et al. |
| 5,723,462 A | 3/1998 | Albaugh et al. |
| 5,750,702 A | 5/1998 | Albaugh et al. |
| 5,804,686 A | 9/1998 | Albaugh et al. |
| 5,817,813 A | 10/1998 | Thurkauf et al. |
| 5,925,770 A | 7/1999 | Albaugh et al. |
| 6,013,650 A | 1/2000 | Thurkauf et al. |
| 6,080,873 A | 6/2000 | Albaugh et al. |
| 6,096,887 A | 8/2000 | Albaugh et al. |
| 6,143,760 A | 11/2000 | Albaugh et al. |
| 6,166,203 A | 12/2000 | Cai et al. |
| 6,177,569 B1 | 1/2001 | Rachwal et al. |
| 6,211,365 B1 | 4/2001 | Albaugh et al. |
| 6,229,017 B1 | 5/2001 | Lui et al. |
| 6,297,256 B1 | 10/2001 | Cai et al. |

(Continued)

FOREIGN PATENT DOCUMENTS

| | | |
|---|---|---|
| AU | 2005204365 A1 | 7/2005 |
| AU | 2005209365 A1 | 8/2005 |

(Continued)

OTHER PUBLICATIONS

Limon, Agenor & Reyes-Ruiz, Jorge & Miledi, Ricardo. (2011). GABA and Glutamate Receptors of the Autistic Brain. 10.5772/20304.*

(Continued)

*Primary Examiner* — Alicia L Otton

(74) *Attorney, Agent, or Firm* — Wolf, Greenfield & Sacks, P.C.

(57) ABSTRACT

The present invention relates to chemical compounds of general formula (I):

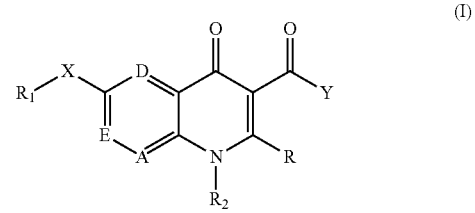

(I)

which may possess useful therapeutic activity in a range of central nervous system disorders, and in particular, anxiety disorders.

9 Claims, No Drawings

(56) References Cited

U.S. PATENT DOCUMENTS

| | | |
|---|---|---|
| 6,353,109 B1 | 3/2002 | Albaugh et al. |
| 6,399,604 B1 | 6/2002 | Albaugh et al. |
| 6,413,956 B1 | 7/2002 | Albaugh et al. |
| 6,414,147 B1 | 7/2002 | Currie et al. |
| 6,423,711 B1 | 7/2002 | Cai et al. |
| 6,423,956 B1 | 7/2002 | Mandella et al. |
| 6,511,987 B1 | 1/2003 | Yuan et al. |
| 6,515,140 B2 | 2/2003 | Albaugh et al. |
| 6,559,163 B2 | 5/2003 | Cai et al. |
| 6,646,124 B2 | 11/2003 | Albaugh et al. |
| 6,656,941 B2 | 12/2003 | Maynard et al. |
| 6,703,393 B2 | 3/2004 | Li et al. |
| 6,720,339 B2 | 4/2004 | Albaugh et al. |
| 6,723,332 B2 | 4/2004 | Cai et al. |
| 6,828,329 B2 | 12/2004 | Cai et al. |
| 7,829,694 B2 | 11/2010 | Kaemmerer et al. |
| 8,293,737 B2 | 10/2012 | Baell et al. |
| 8,551,990 B2 | 10/2013 | Baell et al. |
| 8,614,212 B2 | 12/2013 | Baell et al. |
| 8,906,912 B2 | 12/2014 | Baell et al. |
| 9,023,848 B2 | 5/2015 | Flynn et al. |
| 9,133,188 B2 | 9/2015 | Paul et al. |
| 9,573,945 B2 | 2/2017 | Baell et al. |
| 9,975,892 B2 | 5/2018 | Baell et al. |
| 10,233,181 B2 | 3/2019 | Baell et al. |
| 2002/0151591 A1 | 10/2002 | Villalobos et al. |
| 2004/0082555 A1 | 4/2004 | Villalobos |
| 2005/0009861 A1 | 1/2005 | Villalobos et al. |
| 2005/0182085 A1 | 8/2005 | Defossa et al. |
| 2005/0182086 A1 | 8/2005 | Defossa et al. |
| 2005/0182087 A1 | 8/2005 | Defossa et al. |
| 2010/0105678 A1 | 4/2010 | Baell et al. |
| 2014/0051701 A1 | 2/2014 | O'Connor et al. |
| 2017/0183347 A1 | 1/2017 | Baell et al. |
| 2018/0105523 A1 | 4/2018 | Baell et al. |

FOREIGN PATENT DOCUMENTS

| | | |
|---|---|---|
| AU | 2005209367 A1 | 8/2005 |
| AU | 2005209368 A1 | 8/2005 |
| CA | 1114822 A | 12/1981 |
| EP | 0 3419 90 A2 | 11/1989 |
| EP | 0 531 958 A1 | 3/1999 |
| JP | 50-023036 B | 8/1975 |
| JP | 50-023037 B | 8/1975 |
| JP | 51-032594 A | 3/1976 |
| JP | 55-111486 A | 8/1980 |
| JP | 55-151584 A | 11/1980 |
| JP | 56-115787 A | 9/1981 |
| JP | 56-118081 A | 9/1981 |
| JP | 56-118083 A | 9/1981 |
| JP | 57-026688 A | 2/1982 |
| JP | 57-109790 A | 7/1982 |
| JP | 59-093080 A | 5/1984 |
| JP | 2002-544197 A | 12/2004 |
| JP | 2005-162726 A | 6/2005 |
| JP | 2006-508989 A | 3/2006 |
| WO | WO 2000/68202 A1 | 11/2000 |
| WO | WO 2002/060872 A1 | 8/2002 |
| WO | WO 2002/069948 A1 | 9/2002 |
| WO | WO 2003/045313 A2 | 6/2003 |
| WO | WO 2003/045920 A1 | 6/2003 |
| WO | WO 2003/097564 A2 | 11/2003 |
| WO | WO 2004/048374 A1 | 6/2004 |
| WO | WO 2004/058144 A2 | 7/2004 |
| WO | WO 2004/064721 A2 | 8/2004 |
| WO | WO 2004/083207 A1 | 9/2004 |
| WO | WO 2005/073229 A1 | 8/2005 |
| WO | WO 2005/073230 A1 | 8/2005 |
| WO | WO 2005/073231 A1 | 8/2005 |
| WO | WO 2005/097750 A1 | 10/2005 |
| WO | WO 2006/048146 A1 | 5/2006 |
| WO | WO 2006/060390 A1 | 6/2006 |
| WO | WO 2006/128802 A2 | 12/2006 |
| WO | WO 2007/039172 A1 | 4/2007 |
| WO | WO 2008/021210 A2 | 2/2008 |
| WO | WO 2008/046135 * | 4/2008 .......... C07D 471/04 |
| WO | WO 2008/046135 A1 | 4/2008 |
| WO | WO 2010/135360 A1 | 11/2010 |
| WO | WO 2012/109108 A1 | 8/2012 |

OTHER PUBLICATIONS

International Search Report and Written Opinion for PCT/AU2007/001566, dated Nov. 20, 2007.

International Preliminary Report on Patentability for PCT/AU2007/001566, dated Oct. 1, 2008.

International Search Report and Written Opinion for PCT/AU2012/000223 dated Apr. 4, 2012.

International Preliminary Report on Patentability for PCT/AU2012/000223, dated Sep. 12, 2013.

International Search Report and Written Opinion for PCT/AU2012/000216 dated Mar. 15, 2012.

International Preliminary Report on Patentability for PCT/AU2012/000216, dated Sep. 12, 2013.

International Search Report and Written Opinion for PCT/AU2012/000533 dated May 31, 2012.

International Preliminary Report on Patentability for PCT/AU2012/000533, dated Nov. 21, 2013.

International Search Report and Written Opinion for PCT/AU2013/000991, dated Oct. 11, 2013.

[No Author Listed] Mayo Clinic, "Anxiety." Available at http://www.mayoclinic.com/health/anxiety/DS01187. Last accessed Jan. 4, 2012.

[No Author Listed] Medline Plus, "Autoimmune disorders," National Institutes of Health. Available at http://www.nlm.nih.gov/medlineplus/ency/article/000816.html. Last accessed Jun. 3, 2011.

Abdel-Magid et al., Reductive Amination of Aldehydes and Ketones with Sodium Triacetoxyborohydride. Studies on Direct and Indirect Reductive Amination Procedures(1). J Org Chem. May 31, 1996;61(11):3849-3862.

Berge et al., Pharmaceutical salts. J Pharm Sci. Jan. 1977;66(1):1-19.

Castagné et al., Early behavioral screening for antidepressants and anxiolytics. Drug Dev Res. 2006;67(9):729-742.

Collini et al., The solid phase synthesis of tri-substituted indoles. Tetrahedron Lett. 1997;38(46): 7963-66.

Chopin et al., The benzodiazepine antagonist flumazenil blocks the effects of CCK receptor agonists and antagonists in the elevated plus-maze. Psychopharmacology (Berl). 1993;110(4):409-14.

Chung et al., Trimethylaluminium-Facilitated Direct Amidation of Carboxylic Acids. Synlett. 2011;14:2072-2074.

Cryan et al., The age of anxiety: role of animal models of anxiolytic action in drug discovery. Br J Pharmacol. Oct. 2011;164(4):1129-61. doi: 10.1111/j.1476-5381.2011.01362.x.

Dev et al., Brain sphingosine-1-phosphate receptors: implication for FTY720 in the treatment of multiple sclerosis. Pharmacol Ther. Jan. 2008;117(1):77-93. Epub Sep. 8, 2007.

Fassold et al., A new assay for nerve fiber repulsion. Ann N Y Acad Sci. Apr. 2010;1193:43-7. doi: 10.1111/j.1749-6632.2009.05295.x.

Flynn et al., A novel palladium-mediated coupling approach to 2,3-disubstituted benzo(b)thiophenes and its application to the synthesis of tubulin binding agents. Org Lett. Mar. 8, 2001;3(5):651-4.

Gezginci et al., Antimycobacterial activity of substituted isosteres of pyridine- and pyrazinecarboxylic acids. 2. J Med Chem. May 10, 2001;44(10):1560-3.

Han et al., Solid phase parallel synthesis of highly substituted thiophene derivatives and identification of novel phosphodiesterase-4 (PDE-4) inhibitors. Tetrahedron. 1999;55(39):11669-85.

Heindl et al., Studies on the antibacterial activity of quinolone carboxylic acids. IX. Aza analogs. Di- and trisubstituted 1,4-dihydro-4-oxo-1, 5-naphthyridine-3 carboxylic acids and 1-ethyl-4-pyridone-3 carboxylic acids. European Journal of Medicinal Chemistry. 1977;12(6):549-55. German.

(56) References Cited

OTHER PUBLICATIONS

Heinrichs et al., Brain penetrance, receptor occupancy and antistress in vivo efficacy of a small molecule corticotropin releasing factor type I receptor selective antagonist. Neuropsychopharmacology. Aug. 2002;27(2):194-202.
Johnson et al., Solid phase chemistry approach to the SAR development of a novel class of active site-directed thrombin inhibitors. Tetrahedron. 1999;55:11641-52.
Kaffy et al., Synthesis and biological evaluation of vinylogous combretastatin A-4 derivatives. Org Biomol Chem. Jul. 21, 2005;3(14):2657-60. Epub Jun. 21, 2005.
Maslankiewicz et al., Synthesis and Amination of 4-Chloro-3-quinolinesulfonyl Chloride. Heterocycles. 1994;38(6):1317-31.
Maslankiewicz, From Haloquinolines and Halopyridines to Quinoline- and Pyridinesulfonyl Chlorides and Sulfonamides. Heterocycles. 2007;71(9):1975-90.
Nishimura et al., Conformational analysis of tandospirone in aqueous solution: lead evolution of potent dopamine D4 receptor ligands. Bioorg Med Chem Lett. May 7, 2001;11(9):1141-4.
Pettit et al., Antineoplastic agents 322. Synthesis of combretastatin A-4 prodrugs. Anticancer Drug Des. Jun. 1995;10(4):299-309.
Porsolt et al., Behavioural despair in rats: a new model sensitive to antidepressant treatments. Eur J Pharmacol. Feb. 15, 1978;47(4):379-91.
Soskic et al., QSAR study of 1,8-naphthyridin-4-ones as inhibitors of photosystem II. J Chem Inf Comput Sci. Sep.-Oct. 2001;41(5):1316-21.
Temple et al., Synthesis of potential antimalarial agents. VIII. Azaquinolines. II. Preparation of some 1,5-Naphthyridines and pyrido[3,2-d]pyrimidines. J Heterocyclic Chem. 1970;7(5):1219-22. Abstract Only.
Vercek et al., Heterocycles. 182. Neighboring group interaction in ortho-substituted heterocycles. 2. 1,2,4-Oxadiazolylpyridines and pyrido[2,3-d]pyrimidine 3-oxides. J Org Chem. 1979;44(10):1695-1699.
O'Connor et al., The novel anxiolytic compound BNC210 is a negative allosteric modulator of the alpha 7 nicotinic acetylcholine receptor. Poster presented Nov. 17, 2014. Society for Neuroscience Meeting, Washington, DC. Bionomics and Neurofit SAS, 1 page.
Chahrour et al., Translating genetic and preclinical findings into autism therapies. Dialogues Clin Neurosci. Dec. 2017;19(4):335-343. Review.
Kleppner et al., GABA signalling : therapeutic targets for epilepsy, Parkinson's disease and Huntington's disease. Emerging Therapeutic Targets. 2001;5(2):219-39.
Leclerc et al., Pharmacological therapies for autism spectrum disorder: a review. P T. Jun. 2015;40(6):389-97.
Levene et al., Paradoxical Reactions to Benzodiazepines Who Gets Them and Why? Amer Coll Emer Phys. 2018. 3 pages.
Marrosu et al., Paradoxical reactions elicited by diazepam in children with classic autism. Funct Neurol. Jul.-Sep. 1987;2(3):355-61. Abstract Only.
Paton, Benzodiazepines and disinhibition: a review. Psychiatr Bull R Coll Psychiatr. 2002;26(12):460-2. doi: 10.1192/pb.26.12.460.
Rowlett et al., Different GABAA receptor subtypes mediate the anxiolytic, abuse-related, and motor effects of benzodiazepine-like drugs in primates. Proc Natl Acad Sci U S A. Jan. 18, 2005;102(3):915-20. doi: 10.1073/pnas.0405621102. Epub Jan. 11, 2005.
Shin et al., The effect of midazolam dose and age on the paradoxical midazolam reaction in Korean pediatric patients. Korean J Anesthesiol. Jul. 2013;65(1):9-13. doi: 10.4097/kjae.2013.65.1.9. Epub Jul. 19, 2013.

* cited by examiner

ANXIOLYTIC COMPOUNDS

RELATED APPLICATIONS

The present application is a continuation-in-part of and claims priority under 35 U.S.C. § 120 to U.S. patent application U.S. Ser. No. 15/398,472, filed Jan. 4, 2017, now U.S. Pat. No. 9,975,892, which is a continuation of and claims priority under 35 U.S.C. § 120 to U.S. patent application U.S. Ser. No. 14/533,808, filed Nov. 5, 2014, now U.S. Pat. No. 9,573,945, which is a continuation of and claims priority under 35 U.S.C. § 120 to U.S. patent application U.S. Ser. No. 14/030,808, filed Sep. 18, 2013, now U.S. Pat. No. 8,906,912, which is a continuation of and claims priority under 35 U.S.C. § 120 to U.S. patent application U.S. Ser. No. 13/617,153, filed Sep. 14, 2012, now U.S. Pat. No. 8,551,990, which is a continuation of and claims priority under 35 U.S.C. § 120 to U.S. patent application U.S. Ser. No. 12/311,872, filed Nov. 23, 2009, now U.S. Pat. No. 8,293,737, which is a national stage filing under 35 U.S.C. § 371 of international PCT application, PCT/AU2007/001566, filed Oct. 16, 2007, which claims priority under 35 U.S.C. § 119(e) to U.S. provisional patent application, U.S. Ser. No. 60/851,983, filed Oct. 16, 2006, each of which is incorporated herein by reference in their entirety.

FIELD OF THE INVENTION

The present invention relates generally to chemical compounds and methods for their use and preparation. In particular, the invention relates to chemical compounds which may possess useful therapeutic activity in a range of central nervous system disorders, and in particular, anxiety disorders. The invention also relates to the use of these compounds in methods of therapy and the manufacture of medicaments as well as compositions containing these compounds.

BACKGROUND OF THE INVENTION

γ-Aminobutyric acid (GABA) is one of the major inhibitory amino acid transmitters in the mammalian central nervous system (CNS) and acts by binding to specific receptors in the plasma membrane of both pre- and post-synaptic neurons. The binding of GABA to specific receptors causes the opening of ion channels in the cell membrane which allows either the flow of negatively-charged chloride ions into the cell or positively-charged potassium ions out of the cell. This typically results in a negative change in the transmembrane potential which usually causes hyperpolarisation.

There were once thought to be three types of receptors for GABA in the mammalian CNS, designated A, B, and C. $GABA_A$ and $GABA_C$ receptors are GABA-gated chloride ion-conducting channels while the GABA B receptor is a member of the G-protein receptor superfamily. $GABA_A$ and $GABA_C$ receptors were initially distinguished from one another by their sensitivity to the ligand bicuculline with the former being antagonised by it while the latter were insensitive. However, it has become increasingly clear since the mid-1990s that the $GABA_A$ and $GABA_C$ receptors are simply variants of the same GABA-gated chloride channel. Therefore, these receptors are now denoted by the "$GABA_A$" receptor designation. While varieties of the $GABA_A$ receptor are found all over the CNS, the $GABA_C$ receptors ($GABA_A$ variant also now defined variously as $GABA_{A0r}$) are primarily found in the retina.

The $GABA_A$ receptor is a member of the Cys-loop ligand-gated ion channel superfamily which also includes the glycine, 5-HT3, and nicotinic acetylcholine receptors. Receptors of this superfamily are pentamers with subunits arranged around a central ion-conducting channel. There are 19 different subunit genes—not including alternatively-spliced variants such as the short (S) and long (L) forms of the α1-6, γ1-3, γ2 subunit—divided into eight subunit classes: β1-3, θ, ρ1-2, δ, π, ε (listed according to sequence relatedness). It is presumed that these subunits all arose as a result of gene duplications of an original sequence. Within a class of subunits there is approximately 70% sequence identity, and between subunit classes approximately 30% sequence identity. The majority of $GABA_A$ receptor subtypes in the mammalian brain contain at least one α, β, and γ subunit. Most $GABA_A$ receptors consist of assemblies of these three subunit classes. The most abundantly expressed isoform of the $GABA_A$ receptor in the mammalian brain is composed of α1, β2, and γ2, and the likely stoichiometry is two α, two β and one γ subunit arranged around the ion channel anti-clockwise γ-β-α-β-α as seen from the synaptic cleft. $GABA_A$ receptors of these subtypes are overwhelmingly numerically dominant in the CNS.

Each subunit of the $GABA_A$ receptor has a common structure consisting of a large amino-terminal portion, four transmembrane helices—designated transmembrane (TM) one to four, and a short, cytoplasmic loop toward the carboxy-terminus that is composed of the loop extending between TM3 and TM4. The receptor subunits are arranged pseudo-symmetrically so that the TM2 helix of each subunit lines the central pore. Recent models of the structure of the $GABA_A$ receptor have been based on the crystal structure of the related acetylcholine binding protein.

$GABA_A$ receptors can exist in at least three different conformations: open, closed, and desensitised. Activation of the $GABA_A$ receptor by GABA binding to the GABA site allows chloride ions to flow through the central pore and hyperpolarise the neuron, decreasing the probability that it will propagate an action potential. In this activity, the $GABA_A$ receptor does not differ from any other ligand-gated ion channel. However, up to 14 different ligand binding sites have been proposed to account for the modulation of GABA. Thus among neurotransmitter receptors, $GABA_A$ receptors are unique in view of the fact that their are a large number of ligands that can bind and allosterically modulate their function.

Binding of ligands to the $GABA_A$ receptor can alter the conformation of the $GABA_A$ receptor in such a way as to enhance or diminish the chloride flux in response to GABA binding. Some anesthetics (e.g. etomidate and pentobarbitone) both enhance chloride flow in response to GABA binding as well as activating it directly in the absence of GABA. Other ligands, such as cage convulsants of the picrotoxin type, bind within the central pore of the receptor thus, occluding the channel and preventing chloride flow, an effect which occurs no matter what other ligand subsequently binds. Hence, the neurophysiological effects of GABA result from a conformational change that occurs upon binding of GABA to the $GABA_A$ receptor.

The most widely studied and characterised class of allosteric modulators of the GABA-$GABA_A$ receptor complex are a class of compounds known as benzodiazepines (an example of which is diazepam a 1,4-benzodiazepine, commonly known as Valium®) which interact with the benzodiazepine (BZ)-site on the $GABA_A$ receptor. Possession of a γ subunit and a particular type of a subunit (1, 2, 3, or 5) is required to confer sensitivity to this class of compounds.

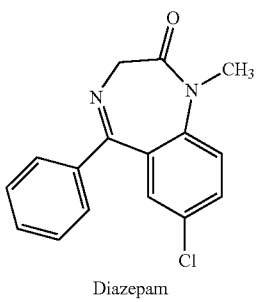

Diazepam

Classical benzodiazepines do not directly open the ion channel, rather they allosterically modify the $GABA_A$ receptor upon binding, potentiating the effect of GABA binding when there is a submaximal concentration of GABA present and thereby increasing hyperpolarizing responses and neuronal inhibition. Benzodiazepines produce systemic effects that include sedation, amnesia, muscle relaxation, and anxiolysis. Hence, these compounds are widely used as anxiolytics, sedative-hypnotics, muscle relaxants, and anti-convulsants. Benzodiazepines were the most widely prescribed class of drugs during the 1970s and, as a group, have one of the largest therapeutic indexes. Although the $GABA_A$ binding site is called the benzodiazepine site, drugs of other types can also bind and allosterically modify the receptor at that site. These include drugs with β-carboline, imidazopyridine, and triazolopyridazine structures. It is believed that compounds acting as BZ agonists at $\alpha_1\beta\gamma_2$, $\alpha_2\beta\gamma_2$ or $\alpha_3\beta\gamma_2$ subtypes will possess desirable anxiolytic activity. Such modulators of the BZ binding site of $GABA_A$ are known herein as "$GABA_A$ receptor agonists".

However, while the 1,4-benzodiazepines are an effective class of anxiolytics they possess the often unwanted side-effect of sedation. It is postulated that at least some of the unwanted sedation experienced by known anxiolytic drugs which act through the BZ binding site is mediated through $GABA_A$ receptors containing the $\alpha_1$-subunit. This has been determined primarily from the effects displayed by the well studied hypnotic agents Alpidem and Zolpidem which are $\alpha_1$-selective $GABA_A$ receptor agonists.

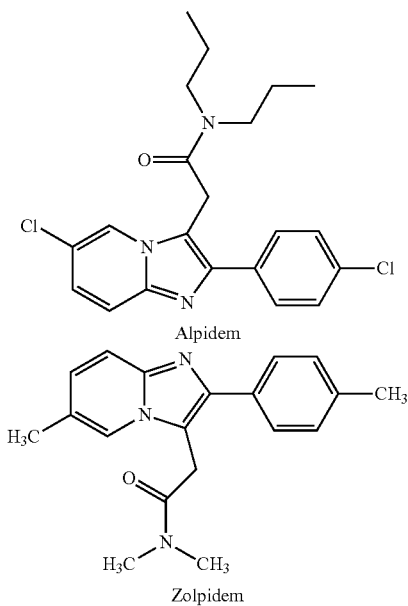

Alpidem

Zolpidem

Thus in order to minimise the sedation effect, while still maintaining effective anxiolytic activity recent research has turned to finding $GABA_A$ receptor agonists which interact more favourably with the $\alpha_2$ and/or $\alpha_3$ subunit than with $\alpha_1$.

SUMMARY OF THE INVENTION

A targeted medicinal chemistry program was initiated, with the aim of producing compounds with improved solubility, metabolic stability, and efficacy.

Briefly, the physicochemical profile and stability in microsome preparations was determined for each compound by standard methods. The strategy used to identify compounds of interest was as follows. Compounds that exhibited improved solubility and stability were then tested for efficacy in the light/dark box, a mouse model of anxiety that was used as the primary efficacy screen. Compounds which performed well in the initial Light/Dark test were then assessed for effects on spontaneous motor activity in mice in a modified Open Field (dark) apparatus. Compounds which exhibited sedative side effects were not tested further. In vivo assessment of the anxiolytic and sedative properties of the compounds allowed for the identification of $GABA_A$ receptor agonists and also for anxiolytic compounds that interacted with other targets, both known and novel.

The present invention provides compounds of formula (I) and salts thereof;

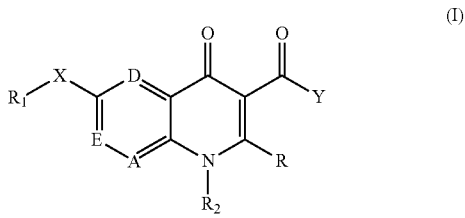

(I)

where A, E, and D are independently selected from CR' (where R' is selected from H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethyl, trihalomethoxy, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, and optionally substituted thioacylamino) or N, and wherein at least one of A, E and D is N;

X represents O or NR" (where R" is selected from H, optionally substituted alkyl, optionally substituted aryl, optionally substituted cycloalkyl, optionally substituted acyl, optionally substituted alkenyl, optionally substituted heterocyclyl, optionally substituted heterocyclyl, optionally substituted heteroaryl, optionally substituted oxysulfinyl, optionally substituted oxysulfonyl, optionally substituted sulfinyl, and optionally substituted sulfonyl);

Y represents OR''' (where R''' is H or optionally substituted alkyl) or $NR_3R_4$;

R represents H or optionally substituted alkyl;

$R_1$ represents optionally substituted cycloalkyl, optionally substituted cycloalkenyl, optionally substituted alkyl, optionally substituted acyl, optionally substituted aryl, optionally substituted heterocyclyl, or optionally substituted heteroaryl;

$R_2$ represents H, optionally substituted cycloalkyl, optionally substituted alkyl, optionally substituted acyl, optionally substituted aryl, optionally substituted alkenyl, optionally substituted heterocyclyl, optionally substituted heteroaryl, optionally substituted oxysulfinyl, optionally substituted oxysulfonyl, optionally substituted sulfinyl, or optionally substituted sulfonyl; and $R_3$ and $R_4$ each independently represent optionally substituted alkyl, or together with the N-atom optionally substituted N-containing heteroaryl or optionally substituted N-containing heterocyclyl.

The present invention also provides a method for treating central nervous system disorders including the step of administering to a patient in need thereof a compound of formula (I) or a pharmaceutically acceptable salt thereof;

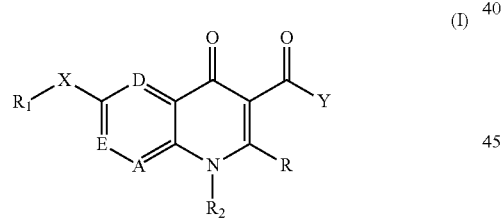

(I)

where A, E, and D are independently selected from CR' (where R' is selected from H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethyl, trihalomethoxy, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, and optionally substituted thioacylamino) or N, and wherein at least one of A, E and D is N;

X represents O or NR" (where R" is selected from H, optionally substituted alkyl, optionally substituted aryl, optionally substituted cycloalkyl, optionally substituted acyl, optionally substituted alkenyl, optionally substituted heterocyclyl, optionally substituted heterocyclyl, optionally substituted heteroaryl, optionally substituted oxysulfinyl, optionally substituted oxysulfonyl, optionally substituted sulfinyl, and optionally substituted sulfonyl);

R represents H or optionally substituted alkyl;

Y represents OR''' (where R''' is H or optionally substituted alkyl) or $NR_3R_4$;

$R_1$ represents optionally substituted cycloalkyl, optionally substituted cycloalkenyl, optionally substituted alkyl, optionally substituted acyl, optionally substituted aryl, optionally substituted heterocyclyl, or optionally substituted heteroaryl;

$R_2$ represents H, optionally substituted cycloalkyl, optionally substituted alkyl, optionally substituted acyl, optionally substituted aryl, optionally substituted alkenyl, optionally substituted heterocyclyl, optionally substituted heteroaryl, optionally substituted oxysulfinyl, optionally substituted oxysulfonyl, optionally substituted sulfinyl or optionally substituted sulfonyl; and $R_3$ and $R_4$ each independently represent optionally substituted alkyl, or together with the N-atom optionally substituted N-containing heteroaryl or optionally substituted N-containing heterocyclyl.

The present invention also provides the use of a compound of formula (I) or a salt thereof:

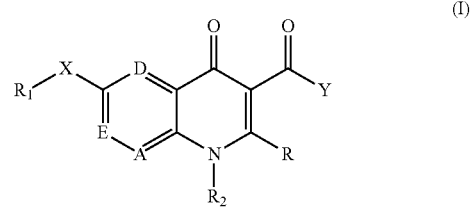

(I)

where A, E, and D are independently selected from CR' (where R' is selected from H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethyl, trihalomethoxy, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, and optionally substituted thioacylamino) or N, and wherein at least one of A, E and D is N;

X represents O or NR" (where R" is selected from H, optionally substituted alkyl, optionally substituted aryl, optionally substituted cycloalkyl, optionally substituted acyl, optionally substituted alkenyl, optionally substituted heterocyclyl, optionally substituted heterocyclyl, optionally substituted heteroaryl, optionally substituted oxysulfinyl, optionally substituted oxysulfonyl, and optionally substituted sulfinyl, optionally substituted sulfonyl);

Y represents OR''' (where R''' is H or optionally substituted alkyl) or $NR_3R_4$;

R represents H or optionally substituted alkyl;

$R_1$ represents optionally substituted cycloalkyl, optionally substituted cycloalkenyl, optionally substituted alkyl, optionally substituted acyl, optionally substituted aryl, optionally substituted heterocyclyl, or optionally substituted heteroaryl;

$R_2$ represents H, optionally substituted cycloalkyl, optionally substituted alkyl, optionally substituted acyl, optionally substituted aryl, optionally substituted alkenyl, optionally substituted heterocyclyl, optionally substituted heteroaryl, optionally substituted oxysulfinyl, optionally substituted oxysulfonyl, optionally substituted sulfinyl, or optionally substituted sulfonyl; and $R_3$ and $R_4$ each independently represent optionally substituted alkyl, or together with the N-atom optionally substituted N-containing heteroaryl or optionally substituted N-containing heterocyclyl, in the manufacture of a medicament for the treatment of central nervous system disorders.

DETAILED DESCRIPTION OF THE INVENTION

The invention is based on the discovery that the compounds of the general formula I, as described in the above Summary of the Invention have useful properties as possible ligands for $GABA_A$ receptors and/or other receptors and biological targets that elicit an anxiolytic effect. Such compounds have significant potential for the treatment of a variety of disorders of the central nervous system, and in particular anxiety disorders.

"Alkyl" refers to monovalent alkyl groups which may be straight chained or branched and preferably have from 1 to 10 carbon atoms or more preferably 1 to 6 carbon atoms. Examples of such alkyl groups include methyl, ethyl, n-propyl, iso-propyl, n-butyl, iso-butyl, n-hexyl, and the like.

"Alkylene" refers to divalent alkyl groups preferably having from 1 to 10 carbon atoms and more preferably 1 to 6 carbon atoms. Examples of such alkylene groups include methylene ($—CH_2—$), ethylene ($—CH_2CH_2—$), and the propylene isomers (e.g., $—CH_2CH_2CH_2—$ and $—CH(CH_3)CH_2—$), and the like.

"Aryl" refers to an unsaturated aromatic carbocyclic group having a single ring (e.g. phenyl) or multiple condensed rings (e.g. naphthyl or anthryl), preferably having from 6 to 14 carbon atoms. Examples of aryl groups include phenyl, naphthyl and the like.

"Arylene" refers to a divalent aryl group wherein the aryl group is as described above.

"Aryloxy" refers to the group aryl-O— wherein the aryl group is as described above.

"Arylalkyl" refers to -alkylene-aryl groups preferably having from 1 to 10 carbon atoms in the alkylene moiety and from 6 to 10 carbon atoms in the aryl moiety. Such arylalkyl groups are exemplified by benzyl, phenethyl and the like.

"Arylalkoxy" refers to the group arylalkyl-O— wherein the arylalkyl group are as described above. Such arylalkoxy groups are exemplified by benzyloxy and the like.

"Alkoxy" refers to the group alkyl-O— where the alkyl group is as described above. Examples include, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkenyl" refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl ($—CH=CH_2$), n-propenyl ($—CH_2CH=CH_2$), iso-propenyl ($—C(CH_3)=CH_2$), but-2-enyl ($—CH_2CH=CHCH_3$), and the like.

"Alkenyloxy" refers to the group alkenyl-O— wherein the alkenyl group is as described above.

"Alkenylene" refers to divalent alkenyl groups preferably having from 2 to 8 carbon atoms and more preferably 2 to 6 carbon atoms. Examples include ethenylene ($—CH=CH—$), and the propenylene isomers (e.g., $—CH_2CH=CH—$ and $—C(CH_3)=CH—$), and the like.

"Alkynyl" refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl ($—C≡CH$), propargyl ($—CH_2C≡CH$), pent-2-ynyl ($—CH_2C≡CCH_2—CH_3$), and the like.

"Alkynyloxy" refers to the group alkynyl-O— wherein the alkynyl groups is as described above.

"Alkynylene" refers to the divalent alkynyl groups preferably having from 2 to 8 carbon atoms and more preferably 2 to 6 carbon atoms. Examples include ethynylene ($—C≡C—$), propynylene ($—CH_2—C≡C—$), and the like.

"Acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein.

"Oxyacyl" refers to groups HOC(O)—, alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

"Amino" refers to the group —NR"R" where each R" is independently hydrogen, alkyl, cycloalkyl, aryl, heteroaryl, and heterocyclyl and where each of alkyl, cycloalkyl, aryl, heteroaryl and heterocyclyl is as described herein.

"Aminoacyl" refers to the group —C(O)NR"R" where each R" is independently hydrogen, alkyl, cycloalkyl, aryl, heteroaryl, and heterocyclyl and where each of alkyl, cycloalkyl, aryl, heteroaryl and heterocyclyl is as described herein.

"Acylamino" refers to the group —NR"C(O)R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Acyloxy" refers to the groups —OC(O)-alkyl, —OC(O)-aryl, —C(O)O-heteroaryl, and —C(O)O-heterocyclyl where alkyl, aryl, heteroaryl and heterocyclyl are as described herein.

"Aminoacyloxy" refers to the groups —OC(O)NR"-alkyl, —OC(O)NR"-aryl, —OC(O)NR"-heteroaryl, and —OC(O)NR"-heterocyclyl where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxyacylamino" refers to the groups —NR"C(O)O-alkyl, —NR"C(O)O-aryl, —NR"C(O)O-heteroaryl, and NR"C(O)O-heterocyclyl where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxyacyloxy" refers to the groups —OC(O)O-alkyl, —O—C(O)O-aryl, —OC(O)O-heteroaryl, and —OC(O)O-heterocyclyl where alkyl, cycloalkyl, aryl, heteroaryl, and heterocyclyl are as described herein.

"Acylimino" refers to the groups —C(NR")—R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Acyliminoxy" refers to the groups —O—C(NR")—R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Oxyacylimino" refers to the groups —C(NR")—OR" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Cycloalkyl" refers to cyclic alkyl groups having a single cyclic ring or multiple condensed rings, preferably incorporating 3 to 11 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, indanyl, 1,2,3,4-tetrahydronapthalenyl and the like.

"Cycloalkenyl" refers to cyclic alkenyl groups having a single cyclic ring or multiple condensed rings, and at least one point of internal unsaturation, preferably incorporating 4 to 11 carbon atoms. Examples of suitable cycloalkenyl groups include, for instance, cyclobut-2-enyl, cyclopent-3-enyl, cyclohex-4-enyl, cyclooct-3-enyl, indenyl and the like.

"Halo" or "halogen" refers to fluoro, chloro, bromo and iodo.

"Heteroaryl" refers to a monovalent aromatic heterocyclic group which fulfils the Hückel criteria for aromaticity (i.e. contains $4n+2\pi$ electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (e.g. pyridyl, pyrrolyl or N-oxides thereof or furyl) or multiple condensed rings (e.g. indolizinyl, benzoimidazolyl, coumarinyl, quinolinyl, isoquinolinyl or benzothienyl). It will be understood that where, for instance, $R_2$ or R' is an optionally substituted heteroaryl which has one or more ring heteroatoms, the heteroaryl group can be connected to the core molecule of the compounds of the present invention, through a C—C or C-heteroatom bond, in particular a C—N bond.

"Heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring. The most preferred heteroatom is nitrogen. It will be understood that where, for instance, $R_2$ or R' is an optionally substituted heterocyclyl which has one or more ring heteroatoms, the heterocyclyl group can be connected to the core molecule of the compounds of the present invention, through a C—C or C-heteroatom bond, in particular a C—N bond.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Heteroarylene" refers to a divalent heteroaryl group wherein the heteroaryl group is as described above.

"Heterocyclylene" refers to a divalent heterocyclyl group wherein the heterocyclyl group is as described above.

"Thio" refers to groups H—S—, alkyl-S—, cycloalkyl-S—, aryl-S—, heteroaryl-S—, and heterocyclyl-S—, where alkyl, cycloalkyl, aryl, heteroaryl and heterocyclyl are as described herein.

"Thioacyl" refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl and heterocyclyl are as described herein.

"Oxythioacyl" refers to groups HO—C(S)—, alkylO—C(S)—, cycloalkylO—C(S)—, arylO—C(S)—, heteroarylO—C(S)—, and heterocyclylO—C(S)—, where alkyl, cycloalkyl, aryl, heteroaryl and heterocyclyl are as described herein.

"Oxythioacyloxy" refers to groups HO—C(S)—O—, alkylO—C(S)—O—, cycloalkylO—C(S)—O—, arylO—C(S)—O—, heteroarylO—C(S)—O—, and heterocyclylO—C(S)—O—, where alkyl, cycloalkyl, aryl, heteroaryl and heterocyclyl are as described herein.

"Phosphorylamino" refers to the groups —NR"—P(O)(R''')(OR"") where R" represents H, alkyl, cycloalkyl, alkenyl, or aryl, R''' represents OR"" or is hydroxy or amino and R"" is alkyl, cycloalkyl, aryl or arylalkyl, where alkyl, amino, alkenyl, aryl, cycloalkyl, and arylalkyl are as described herein.

"Thioacyloxy" refers to groups H—C(S)—O—, alkyl-C(S)—O—, cycloalkyl-C(S)—O—, aryl-C(S)—O—, heteroaryl-C(S)—O—, and heterocyclyl-C(S)—O—, where alkyl, cycloalkyl, aryl, heteroaryl, and heterocyclyl are as described herein.

"Sulfinyl" refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl and heterocyclyl are as described herein.

"Sulfonyl" refers to groups H—S(O)$_2$—, alkyl-S(O)$_2$—, cycloalkyl-S(O)$_2$—, aryl-S(O)$_2$—, heteroaryl-S(O)$_2$—, and heterocyclyl-S(O)$_2$—, where alkyl, cycloalkyl, aryl, heteroaryl and heterocyclyl are as described herein.

"Sulfinylamino" refers to groups H—S(O)—NR"—, alkyl-S(O)—NR"—, cycloalkyl-S(O)—NR"—, aryl-S(O)—NR"—, heteroaryl-S(O)—NR"—, and heterocyclyl-S(O)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Sulfonylamino" refers to groups H—S(O)$_2$—NR"—, alkyl-S(O)$_2$—NR"—, cycloalkyl-S(O)$_2$—NR"—, aryl-S(O)$_2$—NR"—, heteroaryl-S(O)$_2$—NR"—, and heterocyclyl-S(O)$_2$—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfinylamino" refers to groups HO—S(O)—NR"—, alkylO—S(O)—NR"—, cycloalkylO—S(O)—NR"—, arylO—S(O)—NR"—, heteroarylO—S(O)—NR"—, and heterocyclylO—S(O)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfonylamino" refers to groups HO—S(O)$_2$—NR"—, alkylO—S(O)$_2$—NR"—, cycloalkylO—S(O)$_2$—NR"—, arylO—S(O)$_2$—NR"—, heteroarylO—S(O)$_2$—NR"—, and heterocyclylO—S(O)$_2$—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Aminothioacyl" refers to groups R"R"N—C(S)—, where each R" is independently hydrogen, alkyl, cycloalkyl, aryl, heteroaryl, and heterocyclic and where each of alkyl, cycloalkyl, aryl, heteroaryl and heterocyclyl is as described herein.

"Thioacylamino" refers to groups H—C(S)—NR"—, alkyl-C(S)—NR"—, cycloalkyl-C(S)—NR"—, aryl-C(S)—NR"—, heteroaryl-C(S)—NR"—, and heterocyclyl-C(S)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Aminosulfinyl" refers to groups R"R"N—S(O)—, where each R" is independently hydrogen, alkyl, cycloalkyl, aryl, heteroaryl, and heterocyclic and where each of alkyl, cycloalkyl, aryl, heteroaryl and heterocyclyl is as described herein.

"Aminosulfonyl" refers to groups R"R"N—S(O)$_2$—, where each R" is independently hydrogen, alkyl, cycloalkyl, aryl, heteroaryl, and heterocyclic and where each of alkyl, cycloalkyl, aryl, heteroaryl and heterocyclyl is as described herein.

In this specification "optionally substituted" is taken to mean that a group may or may not be further substituted or fused (so as to form a condensed polycyclic group) with one or more groups selected from hydroxyl, acyl, alkyl, alkoxy, alkenyl, alkenyloxy, alkynyl, alkynyloxy, amino, aminoacyl, thio, arylalkyl, arylalkoxy, aryl, aryloxy, carboxyl, acylamino, cyano, halogen, nitro, phosphono, sulfo, phosphorylamino, phosphinyl, heteroaryl, heteroaryloxy, heterocyclyl, heterocyclyloxy, oxyacyl, oxime, oxime ether, hydrazone, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like, and may also include a bond to a solid support material, (for example, substituted onto a polymer resin). For instance, an "optionally substituted amino" group may include amino acid and peptide residues.

In a preferred embodiment two of A, E or D are N and the other is CR'.

Accordingly, preferred compounds of formula (I) are represented by formulae (Ia), (Ib), and (Ic):

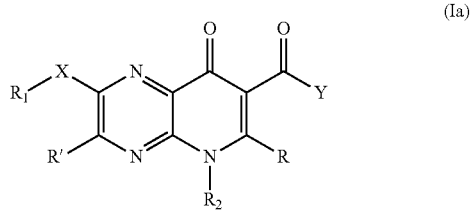

(Ia)

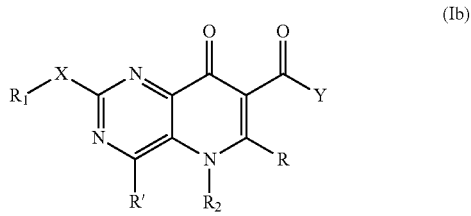

(Ib)

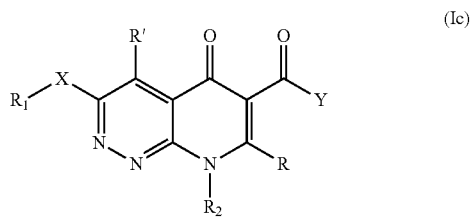

(Ic)

Where R, R$_1$, R$_2$, R', Y and X are as described above for compounds of formula (I).

In a more preferred embodiment only one of A, E and D is N and the other two independently CR'.

Accordingly, more preferred compounds are represented by formulae (Id), (Ie) and (If):

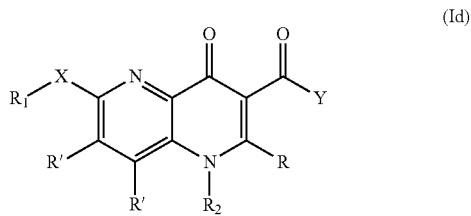

(Id)

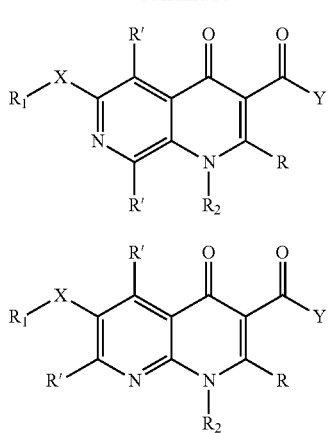

(Ie)

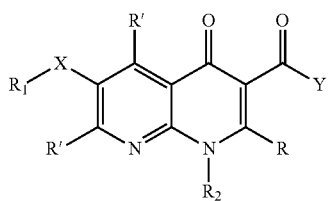

(If)

Where R, $R_1$, $R_2$, R', Y and X are as described above for compounds of formula (I).

In the above embodiments R' in CR' includes the following groups:
hydrogen, halogen, cyano, nitro, and amino
alkyl group, preferably methyl and ethyl;
substituted alkyl group, preferably 1-hydroxyethyl, 1-thioethyl, methoxyiminomethyl, ethoxyiminomethyl, 1-(hydroxyimino)ethyl, 1-(hydroxyimino)propyl, 1-hydrazinoethyl, 1-hydrazinopropyl, hydroxyiminomethyl, 2-oxopropyl, 2-oxobutyl, 3-oxobutyl, 3-oxopentyl, nitromethyl, 1-nitromethyl, and 2-nitroethyl;
aryl group, preferably phenyl and napthyl;
substituted aryl group, preferably halophenyl, aminophenyl, carboxyphenyl, hydroxyphenyl, cyanophenyl, nitrophenyl, trihaloalkylphenyl, and alkylphenyl.
acyl group, preferably formyl acetyl, propionyl, benzoyl (optionally substituted with methyl, methoxy, halogen, nitro, trifluoromethyl or cyano);
alkoxy group, preferably methoxy and ethoxy;
oxyacyl group, preferably methoxycarbonyl, ethoxycarbonyl, propoxycarbonyl, butyloxycarbonyl, isobutyloxycarbonyl;
acyloxy group, preferably acetoxy and propioxy;
substituted arylalkyl group, preferably 1-hydroxybenzyl, and 1-thiobenzyl;
sulfinyl group, preferably methylsulfinyl, ethylsulfinyl, benzene sulfinyl (optionally substituted with methyl, methoxy, halogen, nitro, trifluoromethane or cyano), methoxysulfinyl, ethoxysulfinyl;
sulfonyl group, preferably methylsulfonyl, ethylsulfonyl, benzenesulfonyl (optionally substituted with methyl, methoxy, halogen, nitro, trifluoromethane or cyano), methoxycarbo, trifluoromethane;
oxyacylamino group, preferably methoxycarbonylamido, and ethoxycarbonyl amido;
oxythioacyl group, preferably methoxythiocarbonyl and ethoxythiocarbonyl;
thioacyloxy group, preferably thionoacetoxy and thionopropionoxy;
sulphinylamino group, preferably methylsulfinylamino, ethylsulfinylamino, and benzenesulfinylamino (optionally substituted with methyl, methoxy, halogen, nitro, trifluoromethane or cyano);
amino group, preferably N-methylamino, and N,N'-dimethylamino;
substituted amino groups, preferably residues of L-valine, D-valine, L-alanine, D-alanine, aspartic acid, and alanylserine;
sulphonylamino group, preferably methylsulfonylamino, ethylsulfonylamino and benzene sulfonylamino (optionally substituted with methyl, methoxy, halogen, nitro, trifluoromethane or cyano);
substituted thio group, preferably alkylthio;
oxysulfinylamino group, preferably methoxysulfinylamino and ethoxysulfinylamino;
oxysulfonylamino group, preferably methoxysulfonylamino and ethoxysulfonylamino;
optionally substituted alkenyl group, preferably, 1-propenyl, vinyl, nitrovinyl, cyano vinyl, or trifluorovinyl and styryl (optionally substituted with methyl, methoxy, halogen, nitro, trifluoromethane or cyano); and
alkynyl group, preferably 1-propynyl, ethynyl or trimethylsilylethynyl.

More preferably, where present, CR' is CH.

In a preferred embodiment Y is $NR^3R^4$. In this embodiment preferably one of $R_3$ and $R_4$ is H and the other is selected from optionally substituted alkyl, optionally substituted aryl, optionally substituted $C_{3-7}$ cycloalkyl, optionally substituted heteroaryl, or optionally substituted heterocyclyl. In another preferred embodiment both $R_3$ and $R_4$ are each independently selected from optionally substituted $C_{1-3}$ alkyl.

In a further preferred embodiment Y is $NR^3R^4$ where $R_3$ and $R_4$ together with the N-atom represent an optionally substituted N-containing heteroaryl or optionally substituted N-containing heterocyclyl.

Accordingly, in an even more preferred embodiment the compounds of the present invention are represented by formula (I') or salts thereof

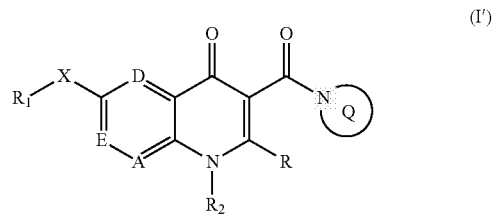

(I')

where A, E, and D are independently selected from CR' (where R' is selected from H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethyl, trihalomethoxy, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, and optionally substituted thioacylamino) or N, and wherein at least one of A, E and D is N;

X represents O or NR" (where R" is selected from H, optionally substituted alkyl, optionally substituted aryl, optionally substituted cycloalkyl, optionally substituted acyl, optionally substituted alkenyl, optionally substituted heterocyclyl, optionally substituted heterocyclyl, optionally substituted heteroaryl, optionally substituted oxysulfinyl, optionally substituted oxysulfonyl, and optionally substituted sulfinyl, optionally substituted sulfonyl);

R represents H or optionally substituted alkyl;

R₁ represents optionally substituted cycloalkyl, optionally substituted alkyl, optionally substituted acyl, optionally substituted aryl, optionally substituted heterocyclyl, or optionally substituted heteroaryl;

R₂ represents H, optionally substituted cycloalkyl, optionally substituted alkyl, optionally substituted acyl, optionally substituted aryl, optionally substituted alkenyl, optionally substituted heterocyclyl, optionally substituted heteroaryl, optionally substituted oxysulfinyl, optionally substituted oxysulfonyl, optionally substituted sulfinyl, or optionally substituted sulfonyl; and Q represents an optionally substituted N-containing heterocyclyl or an optionally substituted N-containing heteroaryl.

In a preferred embodiment two of A, E and D are N and the other CR'. Accordingly, preferred compounds of formula (I') are represented by formulae (I'a), (I'b), and (I'c):

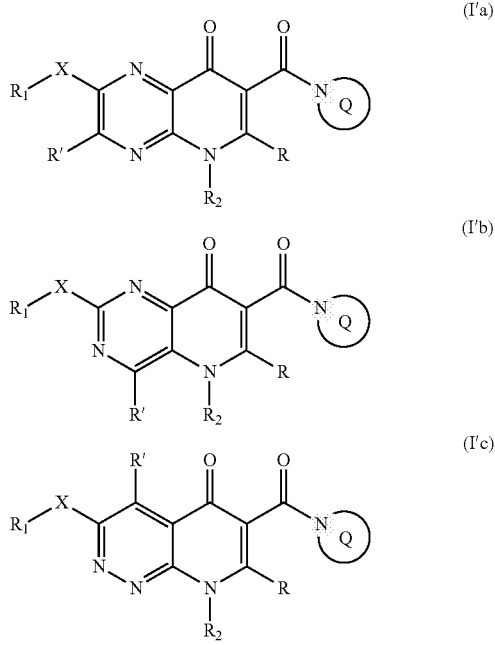

where R, R₁, R₂, Q, R' and X are as defined above.

In a more preferred embodiment only one of A, E, and D is N and the other two independently CR'. Accordingly, more preferred compounds are represented by formulae (I'd), (I'e), and (I'f):

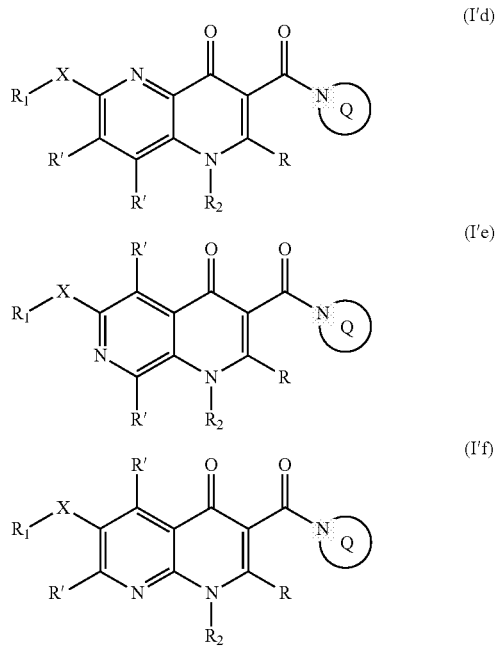

where R, R₁, Q, R₂, R' and X are as defined above.

Preferably, and in respect of compounds of formula (I'), Q represents optionally substituted N-containing heterocyclyl. More preferably, Q represents an N-containing heterocyclyl selected from morpholinyl, piperidyl, piperazinyl, pyrrolidinyl, pyrazolinyl, pyrazolidinyl, imidazolinyl or indolinyl. Most preferably Q represents morpholinyl.

For the compounds of formulae (I) and (I') preferably X is NR" where R" is selected from hydrogen, $C_{1-3}$ alkyl, benzyl, or acetyl. More preferably X is NH.

For the compounds of formulae (I) and (I') preferably R is H or $C_{1-6}$ alkyl. More preferably R is hydrogen or methyl and even more preferably hydrogen.

Preferably for compounds of formulae (I) and (I'), R₁ is selected from optionally substituted alkyl, optionally substituted cycloalkyl, or optionally substituted cycloalkenyl. Preferred substitutents include optionally substituted acyl (for instance, optionally substituted phenylacyl or optionally substituted alkyl acyl), optionally substituted aryl, halogen, COOH, NH₂, mono or dialkyl amino or CF₃. More preferably R₁ is benzofused $C_5$-$C_7$ cycloalkyl (wherein the benzene ring may be optionally substituted). Most preferably, R₁ is indanyl or 1,2,3,4-tetrahydronaphthalenyl.

For the compounds of formulae (I) and (I') preferably R₂ is hydrogen, $C_{1-6}$ alkyl, benzyl or acetyl. More preferably R₂ is $C_{1-3}$ alkyl.

Accordingly, in an even more preferred embodiment the invention provides compounds of formulae (I'd), (I'e), and (I'f) or salts thereof, wherein Q represents N-containing heterocyclyl, X represents NR" (where R" is selected from hydrogen, $C_{1-3}$ alkyl, benzyl or acetyl), R is hydrogen, R₁ represents optionally substituted cycloalkyl or optionally substituted cycloalkenyl, R₂ represents $C_{1-3}$ alkyl and each R' is hydrogen.

The compounds of the present invention can be prepared according to Scheme 1

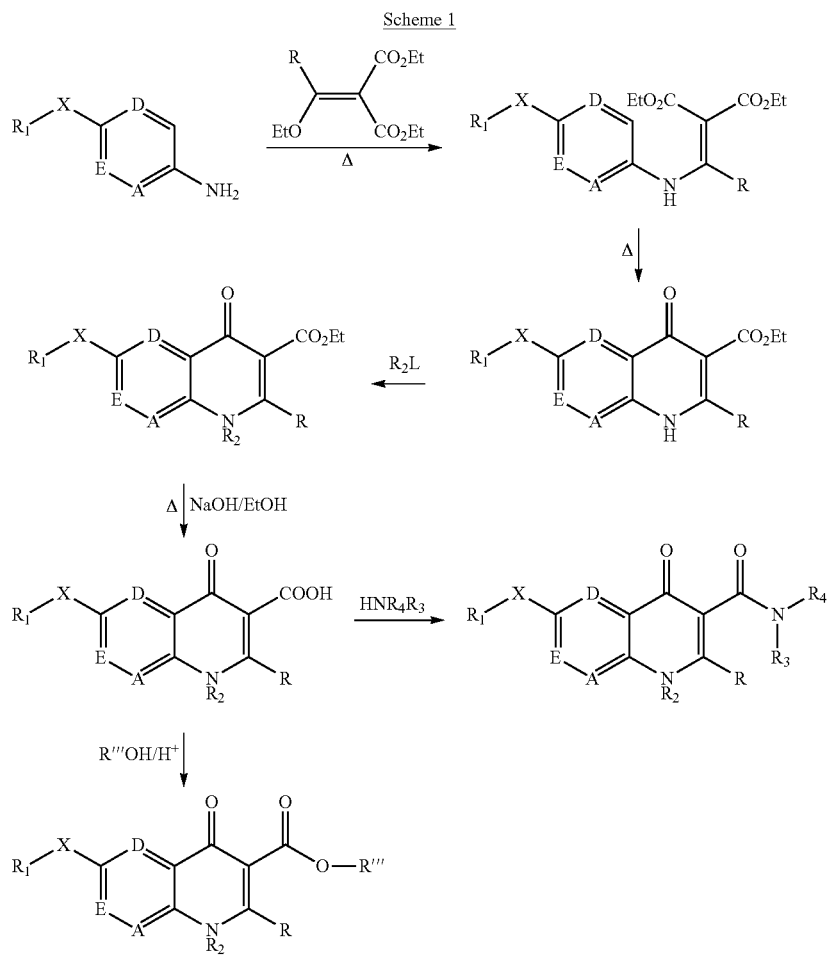

In the above Scheme, preferably only one of A, E, or D is N.

As shown in Scheme 1 an amino substituted N-containing heteroaryl (e.g. a 2-substituted-5-amino-pyridine) may be heated in the presence of a diethyl ethoxymethylene malonate in a suitable solvent (e.g. diethyl ether) to afford the desired diethyl aminomethylene malonate.

This product may then be cyclised at temperatures above 200° C. (for instance in diphenyl ether) to afford the corresponding ring closed product (where Y is OEt). Hydrolysis of the ethyl ester under standard conditions may afford the corresponding carboxylic acid. Alternatively where it is desired to make compounds where $R_2$ is other than H, the ring closed product may be reacted with a suitable electrophilic group (e.g. alkylation with an alkylhalide) under standard conditions.

Coupling of the acid with $HNR_4R_3$ may be achieved under typical peptide coupling conditions. For example, the carboxylic acid can be initially converted to an activated ester with ethyl chloroformate or HBTU in the presence of a suitable non-nucleophilic base (e.g. triethylamine, Hünigs base, etc).

Alternatively other groups where Y is OR''' may be produced by standard ester forming methodology with an alcohol (R'''OH) and suitable acid.

Another approach to the compounds of the present invention is depicted in Scheme 2

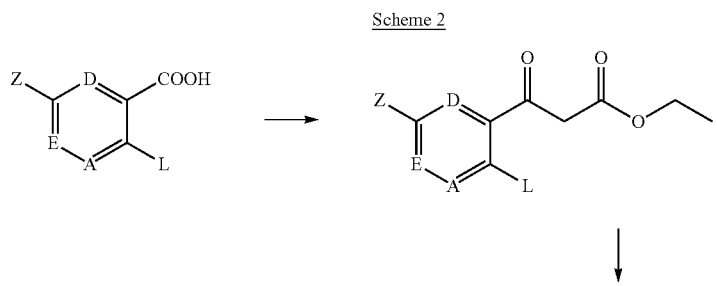

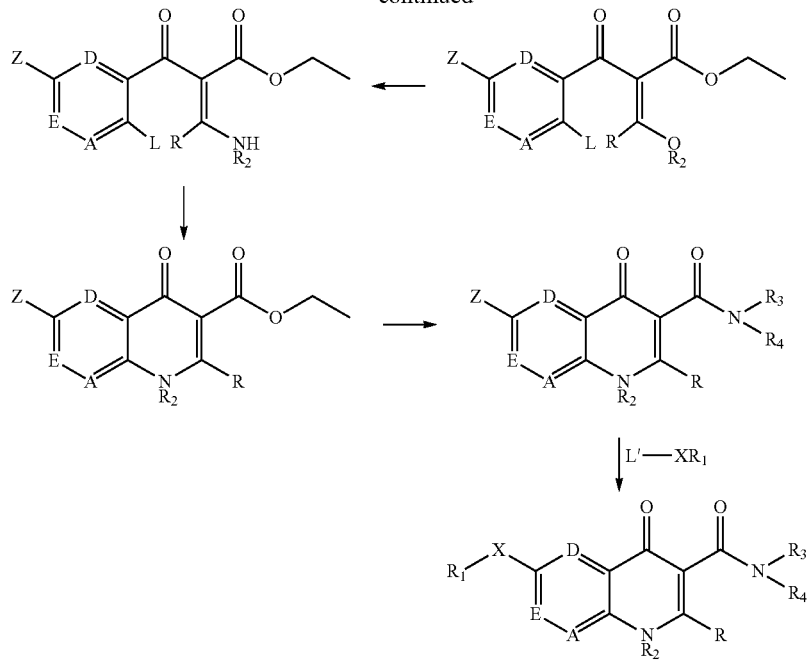

As shown in Scheme 2 a carboxy-substituted N-containing heteroaryl (e.g. a 2,5-disubstituted nicotinic acid) may be converted to the malonate ester by reaction with thionyl chloride and potassium ethyl malonate under standard conditions. The L group depicted in Scheme 2 represents any suitable leaving group which may be halogen, methoxy, tosylate, mesylate, etc. The malonate ester may be reacted with triethylorthoformate in acetic acid followed by the addition of a nucleophilic amine ($HNR_2$) to afford the ethylene amine which may be subsequently cyclised or be promoted to cyclise (e.g. in the presence of a mild base (e.g. $K_2CO_3$)) to afford the ring closed product. Addition of the $XR_1$ group may be accomplished by nucleophilic substitution chemistry with an effective nucleophilie e.g. $^{\ominus}NHR_1$ or $^{\ominus}OR_1$ or may be introduced using palladium catalysed coupling chemistry. Accordingly, Z may be an oxygen based leaving group (or precursor thereof) such as a tosylate or mesylate, or a halogen for instance, Cl, Br, or I.

In Scheme 2 Z may alternatively be $NO_2$. In the final stages of the synthesis (and preferably after the ring closure step) the $NO_2$ group may be reduced to $NH_2$ with the use of, for instance, Raney nickel/$H_2$. The corresponding $NH_2$ group may be reacted with RL' (L' is a leaving group) to produce compounds where —$XR_1$ is —$NHR_1$.

It would be appreciated then that the introduction of the X—$R_1$ group may take place at any convenient stage during the synthetic process and that this applies to both the strategies depicted in Schemes 1 and 2.

The preparation of di- and tri-substituted N-containing heteroaryls as starting materials in the above synthetic procedures may be accomplished using conventional chemistry (see for instance, D. T. Davies, Aromatic Heterocyclic Chemistry, 1993, Oxford Press, New York). Many such starting compounds have also been reported in the literature.

Other compounds of formulae I and I' can be prepared by the addition, removal or modification of existing substituents. This could be achieved by using standard techniques for functional group inter-conversion that are well known in the industry, such as those described in "Comprehensive organic transformations: a guide to functional group preparations" by Larock R. C., New York, VCH Publishers, Inc. 1989.

Examples of functional group inter-conversions are: —C(O)NR*R** from —$CO_2CH_3$ by heating with or without catalytic metal cyanide, e.g. NaCN, and HNR*R** in $CH_3OH$; —OC(O)R from —OH with e.g., ClC(O)R in pyridine; —NC(S)NR*R** from —NHR with an alkylisothiocyanate or thiocyanic acid; —NRC(O)OR* from —NHR with alkyl chloroformate; —NRC(O)NR*R** from —NHR by treatment with an isocyanate, e.g. HN=C=O or RN=C=O; —NRC(O)R* from —NHR by treatment with ClC(O)R* in pyridine; —C(=NR)NR*R** from —C(NR*R**)SR with $H_3NR^+OAc^-$ by heating in alcohol; —C(NR*R**)SR from —C(S)NR*R** with R—I in an inert solvent, e.g. acetone; —C(S)NR*R** (where R* or R** is not hydrogen) from —C(S)$NH_2$ with HNR*R**; —C(=NCN)—NR*R** from —C(=NR*R**)—SR with $NH_2CN$ by heating in anhydrous alcohol, alternatively from —C(=NH)—NR*R** by treatment with BrCN and NaOEt in EtOH; —NR—C(=NCN)SR from —NHR* by treatment with $(RS)_2C$=NCN; —NR**$SO_2$R from —NHR* by treatment with $ClSO_2R$ by heating in pyridine; —NR*C(S)R from —NR*C(O)R by treatment with Lawesson's reagent [2,4-bis(4-methoxyphenyl)-1,3,2,4-dithiadiphosphetane-2, 4-disulfide]; —$NRSO_2CF_3$ from —NHR with triflic anhydride and base, —$CH(NH_2)CHO$ from —$CH(NH_2)C(O)$OR* with Na(Hg) and HCl/EtOH; —$CH_2C(O)OH$ from —C(O)OH by treatment with $SOCl_2$ then $CH_2N_2$ then $H_2O$/$Ag_2O$; —C(O)OH from —$CH_2C(O)OCH_3$ by treatment with PhMgX/HX then acetic anhydride then $CrO_3$; R—OC(O)R* from RC(O)R* by R**$CO_3H$; —$CCH_2OH$ from —C(O)OR* with Na/R*OH; —$CHCH_2$ from —$CH_2CH_2OH$ by the Chugaev reaction; —$NH_2$ from —C(O)OH by the Curtius reaction; —$NH_2$ from —C(O)NHOH with TsCl/base then $H_2O$; —CHC(O)CHR from —CHCHOHCHR by using the Dess-Martin Periodinane regent or $CrO_3/aqH_2SO_4/acetone$; —$C_6H_5CHO$ from —$C_6H_5CH_3$ with $CrO_2Cl_2$; —CHO from —CN with $SnCl_2/HCl$; —CN from —C(O)NHR with $PCl_5$; —$CH_2R$ from —C(O)R with $N_2H_4/KOH$.

During the reactions described above a number of the moieties may need to be protected. Suitable protecting groups are well known in industry and have been described in many references such as Protecting Groups in Organic Synthesis, Greene T W, Wiley-Interscience, New York, 1981.

Without wanting to be bound by theory it is believed that the compounds of the present invention are $GABA_A$ receptor agonists which interact preferentially or more favourably with the α2 and/or α3 subunit than with α1, although their effects may be mediated through interaction with other biomolecules.

The compounds of the present invention may be used in the treatment of a variety of disorders of the central nervous system.

Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; Tourette's syndrome; speech disorders, including stuttering; and disorders of circadian rhythm, e.g. in subjects suffering from the effects of jet lag or shift work. In the diagnostic criteria for Neurodevelopmental Disorders in DSM–5, Autism Spectrum Disorder (ASD) is a new name that reflects a scientific consensus that four previously separate disorders (autistic disorder (autism), Asperger's disorder, childhood disintegrative disorder, and pervasive developmental disorder) are actually a single condition with different levels of symptom severity in two core domains; 1) deficits in social communication and social interaction and 2) restricted repetitive behaviors, interests, and activities (RRBs). Clinically significant anxiety occurs frequently among individuals with autism spectrum disorders.

(ASDs) and when present, is linked to increased psychosocial, familial, behavioral and academic impairment. Up to 80% of children with ASDs experience clinically significant anxiety with high comorbidity rates for social anxiety disorder (30%), generalized anxiety disorder (GAD) (35%), separation anxiety disorder (SAD) (38%) and obsessive compulsive disorder.

In an embodiment the present invention may be used in the treatment of anxiety disorders associated with autism spectrum disorders (ASD).

In an embodiment the present invention may be used in the treatment of social anxiety in patients with ASD.

In an embodiment the present invention may be used in the treatment of anxiety associated with autism spectrum disorders (ASD) wherein the anxiety is an anxiety disorder selected from the group consisting of social anxiety disorder, generalized anxiety disorder, separation anxiety disorder and obsessive compulsive disorder.

Further disorders for which compounds of the invention may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal. Compounds of the invention may be beneficial in enhancing cognition, for example in subjects suffering from dementing conditions such as Alzheimer's disease; and may also be effective as pre-medication prior to anaesthesia or minor procedures such as endoscopy, including gastric endoscopy.

The invention also provides for the use of a compound of formulae (I) and (I') in the manufacture of a medicament for treating disorders of the central nervous system.

There is also provided a method of treatment of disorders of the central nervous system comprising the administration of an effective amount of at least one compound of formula (I) or (I') to a subject in need thereof.

The compounds of the invention may be particularly useful in combination therapy, e.g. combining the treatment with other chemotherapeutic treatments (e.g. muscle relaxants, anticonvulants, hypnotics, anaesthetics, analgesics or other anxiolytics, etc).

It will be understood that the compounds of the invention can be used in the treatment of any disease state which may be ameliorated by modulation of the $GABA_A$ receptor complex.

The compounds of the invention are administered to the subject in a treatment effective amount. As used herein, a treatment effective amount is intended to include at least partially attaining the desired effect, or delaying the onset of, or inhibiting the progression of, or halting or reversing altogether the onset or progression of the particular disease of condition being treated.

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 1 g per kg of body weight per dosage. The dosage may be in the range of 1 μg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another preferred embodiment, the dosage may be in the range of 1 mg to 100 mg per kg of body weight per dosage, such as up to 50 mg per body weight per dosage.

Suitable dosage amounts and dosing regimens can be determined by the attending physician and may depend on the particular condition being treated, the severity of the condition as well as the general age, health and weight of the subject.

The active ingredient may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Preferably, the compounds of the present invention may be administered to a subject as a pharmaceutically acceptable salt. It will be appreciated however that non-pharmaceutically acceptable salts also fall within the scope of the present invention since these may be useful as intermediates in the preparation of pharmaceutically acceptable salts. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In particular, the present invention includes within its scope cationic salts e.g. sodium or potassium salts, or alkyl esters (e.g. methyl, ethyl) of the phosphate group.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

It will be appreciated that any compound that is a prodrug of a compound of formula (I) or (I') is also within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group (for instance at the CR' position) is converted into an ester, such as an acetate or phosphate ester, or where a free amino group is (for instance at the CR' position) converted into an amide (e.g. α-amino acid amide). Procedures for esterifying, e.g. acylating, the compounds of the invention are well known in the art and may include treatment of the compound with an appropriate carboxylic acid, anhydride or chloride in the presence of a suitable catalyst or base. A particularly preferred prodrug is a disodium phosphate ester. The disodium phosphate ester may be prepared in accordance with the methodology described in Pettit, G. R., et al, *Anticancer Drug Des.*, 1995, 10, 299.

The compounds of the invention may be in crystalline form either as the free compounds or as solvates (e.g. hydrates) and it is intended that both forms are within the scope of the present invention. Methods of solvation are generally known within the art.

It will also be recognised that compounds of the invention may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be prepared by asymmetric synthesis, for example using chiral intermediates, or mixtures may be resolved by conventional methods, e.g., chromatography, or use of a resolving agent.

Furthermore, depending on the substitution pattern the compounds of the present invention may be capable of undergoing tautomerism. Accordingly, all possible tautomers of a compound of the present invention fall within the scope and spirit of the invention.

The synthetic methods and processes described herein to prepare the compounds of the present invention are amenable to solid phase synthetic techniques and/or combinatorial chemistry to produce individual compounds or libraries of compounds.

Traditionally, drug candidates have been synthesised individually, this being a time consuming and laborious process if the synthetic sequence contains even just a few steps and large numbers of compounds are to be evaluated for their biological activity. Combinatorial synthesis is an emerging technique for effecting the generation of large libraries of molecules and has been successfully exploited in the synthesis and evaluation of small organic libraries. These libraries and their starting substrates may exist as molecules in free solution or preferably, linked to a solid support, for example, beads, pins, microtitre plates (wells) or microchips which can be polymeric, glass, silica or other suitable substrate. Chemical diversity can be achieved by either parallel or split (split and mix) syntheses wherein each step has the potential to afford a multitude of compounds. Solution phase libraries may be prepared via parallel syntheses wherein different compounds are synthesised in separate reaction vessels in parallel, often in an automated fashion. Alternatively, attachment of the individual components employed in a synthetic sequence to an appropriate solid phase support allows for the further creation of chemical diversity by utilising not only parallel synthesis but also split synthesis wherein the solid support containing the compounds prepared in the prior step can be split into a number of batches, treated with the appropriate reagent and recombined.

The substrates can be attached to a solid support surface by any linkers known in the art. The linkers may be any component capable of being cleaved to release the substrate or final compound from the support.

Preferably, the solid support is a polymer support. Examples of polymeric supports currently used in solid phase synthesis include: alkenyl resins: e.g. REM resins; BHA resins: e.g. benzhydrylamine (polymer-bound hydrochloride, 2% crosslinked), benzhydryl chloride (polymer bound); Br-functionalised resins: e.g. brominated PPOA resin, brominated Wang resin; Chloromethyl resins: e.g. 4-methoxybenzhydryl chloride (polymer bound); CHO-functionalised resins: e.g. indole resin, formylpolystyrene; Cl-functionalised resins: e.g. Merrifield's resin, chloroacetyl (polymer bound); $CO_2H$-functionalised resins: e.g. carboxypolystyrene; I-functionalised resins: e.g. 4-iodophenol (polymer bound); Janda Jels™; MBHA resins: e.g. 4-methylbenzhydrylamine hydrochloride (polymer bound), 4-hydroxymethylbenzoic acid-4-methyl benzhydrylamine (polymer bound); Amine-functionalised resins: e.g. (aminomethyl)polystyrene, PAL resin, Sieber amide resin; Nitrophenyl carbonate resins: e.g. 4-nitrophenyl carbonate (polymer bound); OH-functionalised resins: e.g. 4-benzyloxybenzyl alcohol (polymer bound); Hydroxy methyl resins: e.g. benzyl alcohol (polymer bound); HMBA resin; Oxime resins; Rink acid resin; Triazine-based resin; Trityl amine resins; Trityl resins: e.g. trityl-chloride (polymer bound), 2-chlorotrityl alcohol, 1,3-diaminepropane trityl.

Thus, individual compounds or libraries of compounds can be synthesised by initially attaching the first compound substrate to a solid support surface which can be performed by providing a plurality of solid support surfaces, suitably derivatising each of the surfaces with groups capable of reacting with either the compound substrate or a linker moiety attached thereto. The various support surfaces with the attached first compound substrate can then be subjected to various reaction conditions and second compound substrates to provide a library of attached compounds, which may, if necessary, be reacted further with third and subsequent compound substrates or varying reactions conditions. Attachment and detachment of substrates and products can be performed under conditions similar to those as described in Johnson, M. G., et al., *Tetrahedron*, 1999, 55, 11641; Han Y., et al. *Tetrahedron* 1999, 55, 11669; and Collini, M. D., et al., *Tetrahedron Lett.*, 1997, 58, 7963.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Certain embodiments of the invention will now be described with reference to the following examples which are intended for the purpose of illustration only and are not intended to limit the scope of the generality hereinbefore described.

EXAMPLES

Synthetic Protocols

Example 1

Preparation of Morpholino 6-(2,3-dihydro-1H-inden-2-yl)amino-1-ethyl-1,4-dihydro-4-oxo-1,8-naphthyridine-3-carboxamide (Example 1)

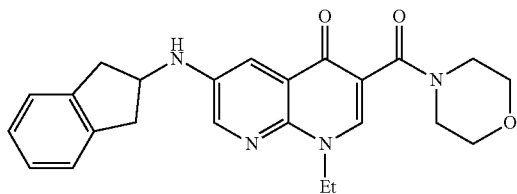

a) 2-Hydroxy-5-nitronicotinic Acid

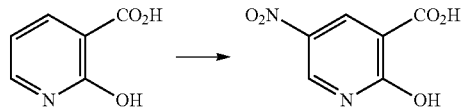 [SMILES: O=C(O)c1cccnc1O ; O=C(O)c1cc([N+](=O)[O-])cnc1O]

To 2-hydroxynicotinic acid (3.6 mmol) in sulfuric acid (30% free $SO_3$, 2 ml) was added sodium nitrate (7.2 mmol) portionwise over 20 min. The solution was allowed to stir for 20 h at room temperature. The solution was then poured onto ice-water and the precipitate that formed was filtered off, washed with water and dried in a vacuum oven to afford a pale yellow solid (45%).

ESIMS: M−1: 183
$^1$H NMR (300 MHz, DMSO) δ 8.94 (1H, d, H-4), 8.67 (1H, d, H-6).

b) 2-Chloro-5-nitronicotinic Acid

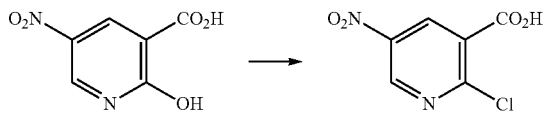 [SMILES: O=C(O)c1cc([N+](=O)[O-])cnc1O ; O=C(O)c1cc([N+](=O)[O-])cnc1Cl]

2-Hydroxy-5-nitronicotinic acid (2.7 mmol) in a mixture of N,N-dimethylformamide (2.7 mmol) and thionyl chloride (5 ml) was heated at 80° C. for 1 h. The mixture was allowed to cool and concentrated in vacuo. To the resulting residue was added ice-water (20 ml) and with vigorous stirring a precipitate formed. The precipitate was filtered off and dried in a vacuum oven to give a white solid (68%).

ESIMS: M−1: 201.
$^1$H NMR (300 MHz, DMSO) δ 9.30 (1H, d, H-4), 8.83 (1H, d, H-6).

c) 2-Methoxy-5-nitro-nicotinic Acid

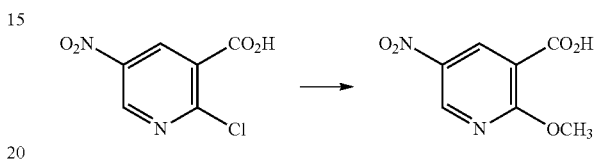

To 2-chloro-5-nitronicotinic acid (1.0 mmol) in methanol was added a solution of sodium methoxide in methanol (2.4 mmol, freshly prepared from sodium metal in methanol). The solution was refluxed for 2 h and the mixture was allowed to cool and concentrated in vacuo. To the resulting residue was added 10% citric acid solution (20 ml) and the solution extracted with ethyl acetate (20 ml). The organic layer was dried ($MgSO_4$) and concentrated in vacuo. The residue was crystallised from water to give a yellow-white solid (73%).

ESIMS: M−1: 197.
$^1$H NMR (300 MHz, DMSO) δ 9.30 (1H, d, H-4), 8.83 (1H, d, H-6), 4.05 (3H, s, $OCH_3$).

d) Preparation of Ethyl 3-oxo-3-(5-nitro-2-methoxy-pyridin-3-yl)propionate

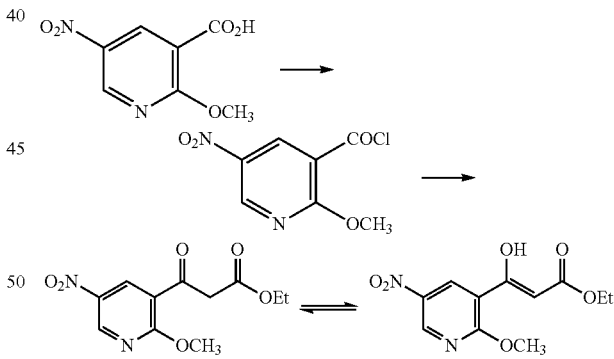

2-Methoxy-5-nitronicotinic acid (36 mmol) and phosphorous pentachloride (72 mmol) were heated at 100° C. for 2 h. The excess reagent was removed in vacuo to give an oily residue.

To a solution of ethyl potassium malonate (75.6 mmol) and triethylamine (72 mmol) in acetonitrile (110 ml) was added magnesium chloride (90 mmol) portionwise over 10 min. This solution was allowed to stir for 8 h at 35° C. To this solution was added dropwise a solution of the pyridyl chloride (from above) in acetonitrile (15 ml) at 0° C. over 20 min. The solution was allowed to warm to room temperature and stirred for 20 h. To this solution was added diethyl ether (100 ml) and 1N hydrochloric acid solution until the pH 5-6 was reached. The two layers were separated and the organic layer was washed with water (100 ml). The organic layer was then dried (MgSO$_4$) and concentrated in vacuo. The resulting residue was then subjected to column chromatography eluting with dichloromethane to afford a clear oily liquid (78%). The NMR spectrum of this compound showed evidence of ketone-enol tautomerism.

ESIMS: M−1: 267.

$^1$H NMR (300 MHz, DMSO) δ 9.17 (d, 0.6H), 9.05 (d, 0.4H), 8.96 (d, 0.4H), 8.94 (d, 0.6H), 6.20 (s, 0.4H), 4.31-4.13 (m, 5H, OMe+OCH$_2$), 3.99 (s, 1.2H), 1.33 (t, 3×0.4H), 1.22 (t, 3×0.6H).

e) Ethyl 1-ethyl-1,4-dihydro-6-nitro-4-oxo-1,8-naphthyridine-3-carboxylate

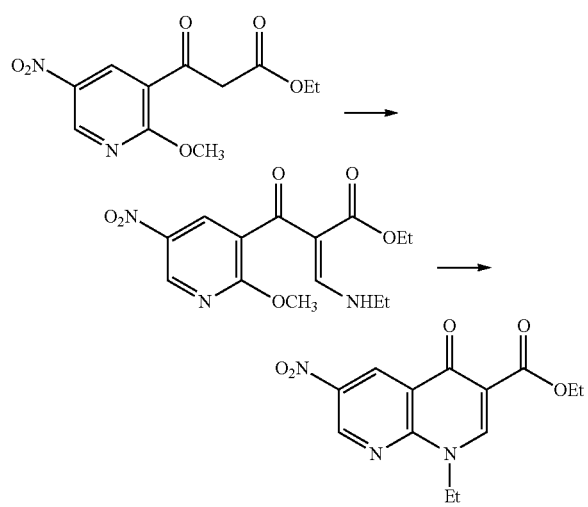

The pyridyl malonate (18 mmol) and triethylorthoformate (23.4 mmol) in acetic anhydride (8 ml) were refluxed for 1 h. The solution was allowed to cool and the excess acetic anhydride was distilled off in vacuo. To the resulting residue in acetonitrile (40 ml) was added dropwise ethylamine (36 mmol) in diethyl ether (20 ml) and the solution was allowed to stir for 5 h at room temperature. The solution was then allowed to cool and was concentrated in vacuo. The residue was dissolved in dichloromethane (60 ml) and washed with water (2×60 ml). The organic layer was then dried (MgSO$_4$) and concentrated in vacuo. The resulting residue was subjected to column chromatography eluting with 100% dichloromethane, and then 2% methanol/dichloromethane to give a white solid (78%).

ESIMS: M+1: 292.

$^1$H NMR (300 MHz, CDCl$_3$) δ 9.50 (1H, d, H-5), 9.44 (1H, d, H-7), 8.66 (1H, s, H-2), 4.53 (2H, q, OCH$_2$), 4.39 (2H, q, NCH$_2$), 1.51 (3H, t, OCH$_2$CH$_3$), 1.40 (3H, t, NCH$_2$CH$_3$).

f) Ethyl 1-ethyl-1,4-dihydro-6-amino-4-oxo-1,8-naphthyridine-3-carboxylate

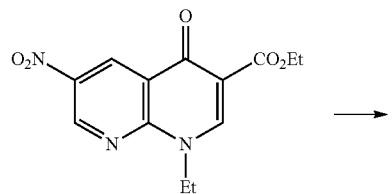

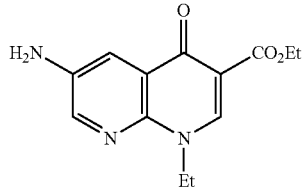

The naphthyridine (1.7 mmol) in N,N-dimethyl formamide (10 ml) was hydrogenated over Raney nickel (0.17 mmol) for 4 h at rt. The mixture was filtered through Celite and washed with tetrahydrofuran. The filtrate was evaporated to dryness. Crystallisation from ethanol obtained the residue as a pale yellow solid (67%).

ESIMS: M+1: 262.

$^1$H NMR (300 MHz, DMSO) δ 8.65 (1H, s, ArH), 8.22 (1H, d, J=2.9 Hz, ArH), 7.62 (1H, d, J=2.9 Hz, ArH), 5.76 (2H, s, NH$_2$), 4.39 (2H, q, J=6.9 Hz, OCH$_2$), 4.17 (2H, q, J=7.2 Hz, NCH$_2$), 1.24 (3H, t, J=6.9 Hz, OCH$_2$CH$_3$), 1.23 (3H, t, J=7.0 Hz, NCH$_2$CH$_3$).

g) Ethyl 6-(2,3-dihydro-1H-inden-2-ylamino)-1-ethyl-1,4-dihydro-4-oxo-1,8-naphthyridine-3-carboxylate

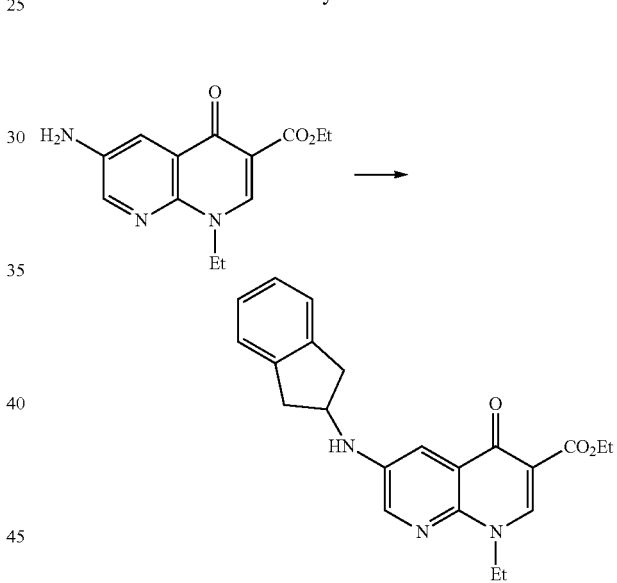

A stirred solution of the 6-aminonaphthyridinone above (0.1 mmol), sodium sulfate (1.0 mmol), 2-indanone (0.15 mmol) and AcOH (7.5 ml) in dichloroethane (30 ml) under a nitrogen atmosphere was allowed to mature for 15 mins at room temperature. Sodium triacetoxyborohydride (0.15 mmol) was then added in one portion and the solution was allowed to stir for 4 h at rt (the reaction was monitored by TLC). A second addition of sodium sulfate (1.0 mmol), 2-indanone (0.15 mmol) and sodium triacetoxyborohydride (0.15 mmol) and stirring overnight was required to drive the reaction to completion. The reaction mixture was quenched with 10% sodium hydrogen carbonate solution and dichloromethane added to dilute the solution. The organic layer was separated from the aqueous layer and the organic layer dried (MgSO$_4$). The organic layer was concentrated in vacuo and the resulting residue subjected to silica column chromatography, gradient-eluting with 100% dichloromethane and then 1% MeOH/dichloromethane to give an oily residue. The residue was triturated using diethyl ether and the solid was filtered off at the pump to afford a pale yellow solid (78%).

ESIMS: M+1: 378.

$^1$H NMR (300 MHz, CDCl$_3$) δ 8.64 (1H, s, H-2), 8.30 (1H, d, H-5), 7.55 (1H, d, H-7), 7.23-7.10 (4H, m, 4×ArH), 6.69 (1H, d, NH), 4.41 (2H, q, OCH$_2$), 4.38-4.23 (1H, m, NCH), 4.17 (2H, q, NCH$_2$), 3.32 (2H, dd, CHC$\underline{H}_2$), 2.81 (2H, dd, CHC$\underline{H}_2$), 1.32 (3H, t, OCH$_2$C$\underline{H}_3$), 1.25 (3H, t, NCH$_2$C$\underline{H}_3$).

h) 6-(2,3-dihydro-1H-inden-2-ylamino)-1-ethyl-1,4-dihydro-4-oxo-1,8-naphthyridine-3-carboxylic Acid

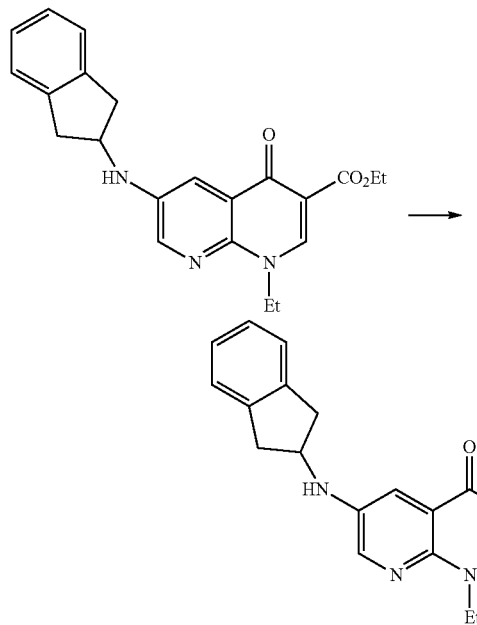

To the naphthyridine above (0.29 mmol) in EtOH (2.5 mL) was added 2N NaOH in water (12.5 mL) at room temperature. The solution was then allowed to stir for 2 h at 90° C. The organic solvent was then removed in vacuo and the remaining aqueous solution was acidified with 10% citric acid solution. The solid that formed was filtered off at the pump and washed with water. This solid was then dried in a vacuum oven to obtain a pale yellow solid (90% yield).

ESIMS: M+1: 350.

$^1$H NMR (300 MHz, DMSO-d$_6$) δ 8.96 (1H, s, H-2), 8.48 (1H, d, H-5), 7.55 (1H, d, H-7), 7.25-7.12 (4H, m, 4×ArH), 7.02 (1H, d, NH), 4.58 (2H, q, NCH$_2$), 4.36-4.31 (1H, m, NCH), 3.32 (2H, dd, CHC$\underline{H}_2$), 2.83 (2H, dd, CHC$\underline{H}_2$), 1.36 (3H, t, NCH$_2$C$\underline{H}_3$).

i) Morpholino 6-(2,3-dihydro-1H-inden-2ylamino)-1-ethyl-1,4-dihydro-4-oxo-1,8-naphthyridine-3-carboxamide

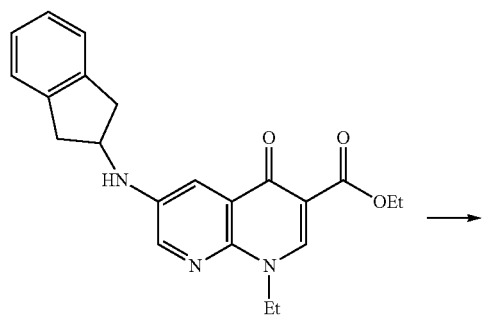

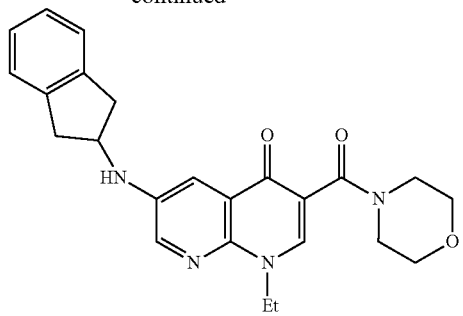

Trimethylaluminium (0.8 mmol, 2M in toluene) was added dropwise to a stirred solution of morpholine (0.8 mmol) in dichloromethane (5 ml). The mixture was stirred for 15 mins and then the naphthyridine (0.4 mmol) in dichloromethane (5 ml) was added. The mixture was then stirred for 20 h at 35° C. The mixture was cooled and then quenched by adding 2 N hydrochloric acid (10 ml) dropwise. The organic layer was then separated, dried (MgSO$_4$) and concentrated in vacuo. The resulting residue was triturated with diethyl ether to give a white solid (78%).

ESIMS: M+1: 419.

$^1$H NMR (300 MHz, CDCl$_3$) δ 8.16 (1H, d, ArH), 8.04 (1H, s, ArH), 7.76 (d, 1H, ArH), 7.24-7.12 (m, 4H, ArH), 4.47-4.33 (4H, m-complex, N$\underline{H}$—C$\underline{H}$+C$\underline{H}_2$CH$_3$), 3.75 (s, 6H, morpholino), 3.42-3.35 (m-complex, 4H, morpholino+CHC$\underline{H}_2$), 2.87 (dd, 2H, CHC$\underline{H}_2$), 1.43 (t, 3H, CH$_3$).

Example 2

Preparation of Morpholino 6-(2,3-dihydro-1H-inden-2-ylamino)-1-ethyl-1,4-dihydro-4-oxo-1,5-naphthyridine-3-carboxamide (Example 2)

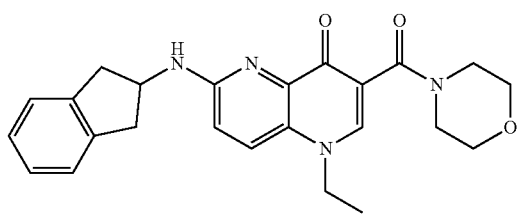 [SMILES: CCn1cc(C(=O)N2CCOCC2)c(=O)c2nc(NC3Cc4ccccc4C3)ccc21]

a) N-(2,3-Dihydro-1H-inden-2-yl)-5-nitropyridin-2-amine

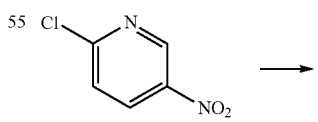

A mixture of 2-chloro-5-nitropyridine (4 g) and N,N-diisopropylethylamine (3 ml) was heated under reflux in dry ethanol (100 ml) for 2 h. The reaction mixture was cooled to 0° C., the solid which separated was filtered off washed with little cold ethanol, dried to give the product (6.25 g, 88%).

$^1$H NMR (300 MHz, CDCl$_3$) δ 8.98 (1H, s, H-6), 8.23 (1H, d, H-4), 7.26-7.17 (4H, m, Ar), 6.43 (1H, d, H-3), 6.12 (1H, bs, NH), 4.71 (1H, bs, NCH), 3.44 (2H, dd, CHC$\underline{H}_2$), 2.93 (2H, dd CHC$\underline{H}_2$).

ESIMS: M+1: 256.

b) N$^2$-(2,3-Dihydro-1H-inden-2-yl)pyridine-2,5-diamine & Diethyl 2-((6-(2,3-dihydro-1H-inden-2-ylamino)pyridine-3-ylamino)methylene)malonate

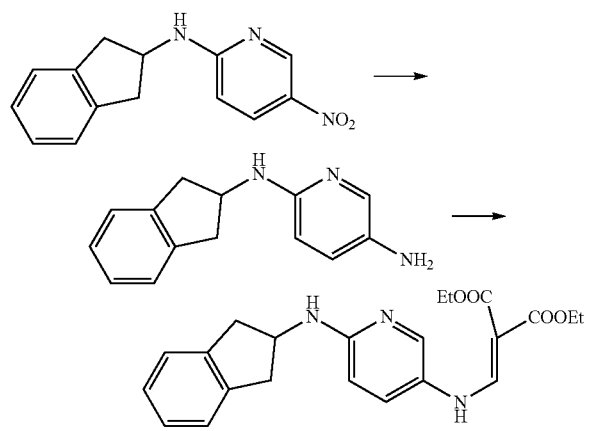

A mixture of N-(2,3-dihydro-1H-inden-2-yl)-5-nitropyridin-2-amine (5.5 g) and Raney Nickel (50 mg) was stirred in DMF (30 ml) under hydrogen overnight. The reaction mixture was filtered through celite and the solvent removed in vacuo, giving as a residue crude N$^2$-(2,3-dihydro-1H-inden-2-yl)pyridine-2,5-diamine, which was on-reacted without further characterization other than ascertaining that the compound was one spot by tlc with the expected molecular weight (M+1) of 226.

A crude mixture of N$^2$-(2,3-dihydro-1H-inden-2-yl)pyridine-2,5-diamine (5 g) and diethyl ethoxymethylenemalonate (5.5 g) was heated under reflux in dry diethyl ether (50 ml) for 1 h. The reaction mixture was then cooled to room temperature, and solvent removed under reduced pressure and the remaining residue finally recrystallised from acetonitrile to give the diethyl 2-((6-(2,3-dihydro-1H-inden-2-ylamino)pyridin-3-ylamino)methylene)malonate (6 g).

$^1$H NMR (300 MHz, DMSO-d$_6$) δ 10.58 (1H, d, 2-N$\underline{H}$CH), 8.15 (1H, d, 5-NHC$\underline{H}$), 8.02 (1H, s, Ar), 7.45 (1H, dd, Ar), 7.20-7.10 (4H, m, Ar), 6.49 (1H, d, 2-NH), 4.51 (1H, m, 2-NHC$\underline{H}$), 6.16-4.04 (4H, 2q, 2×OCH$_2$), 3.44 (2H, dd, CHC$\underline{H}_2$), 2.93 (2H, dd CHC$\underline{H}_2$), 1.24-1.16 (6H, 2t, OCH$_2$C$\underline{H}_3$).

ESIMS: M+1: 396.

c) Ethyl 6-(2,3-dihydro-1H-inden-2-yl)amino-1,4-dihydro-4-oxo-1,5-naphthyridine-3-carboxylate

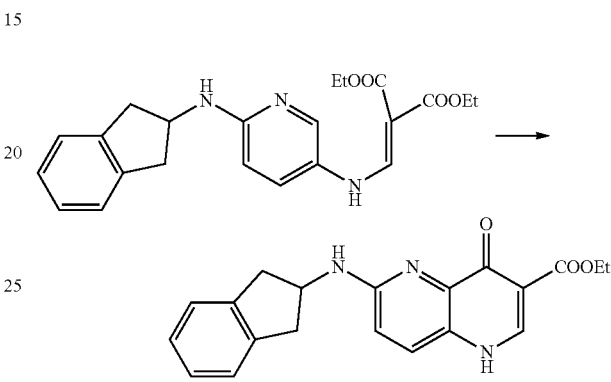

A solution of diethyl 2-((6-(2,3-dihydro-1H-inden-2-yl) amino-pyridin-3-ylamino)methylene)malonate (1.3 g) in dichloromethane (10 ml) was added very carefully into pre-heated (230° C.) diphenyl ether (20 ml) with stirring and heating was continued with stirring for another 20 min after addition had been completed. This was then allowed to cool to room temperature, petroleum ether (200 ml) was added, and the solid which separated was filtered off dried to give the crude product (600 mg), which was on-reacted without further characterization other than ascertaining that the compound was one spot by tlc with the expected molecular weight (M+1) of 350.

d) Ethyl 6-(2,3-dihydro-1H-inden-2-ylamino)-1-ethyl-1,4-dihydro-4-oxo-1,5-naphthyridine-3-carboxylate

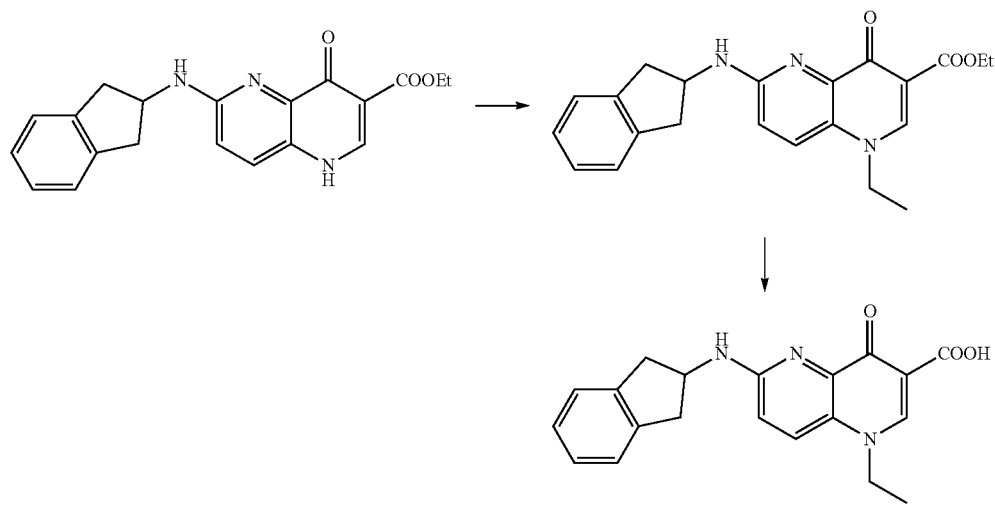

A mixture of ethyl 6-(2,3-dihydro-1H-inden-2-ylamino)-1,4-dihydro-4-oxo-1,5-naphthyridine-3-carboxylate (600 mg), iodoethane (1 g) and potassium carbonate (600 mg) were heated at 90° C. in DMF (20 ml) overnight. After a standard ethyl acetate/aqueous work-up, the residue from the evaporated organic layer (crude cyclized ethyl ester), was heated at 80° C. in a mixture of ethanol (25 ml) and 2M NaOH (10 ml) for 2 h. This was then cooled to room temperature, aq. HCl was added to adjust the pH to 5, at which point the product precipitated and was filtered off, washed with water, and dried to give the crude product (~350 mg).

$^1$H NMR (300 MHz, DMSO-$d_6$) δ 8.78 (1H, s, H-2), 8.10 (1H, dd, H-8), 7.71 (1H, d, H-7), 7.24-7.11 (4H, m, Ar), 7.06 (1H, d, NH), 4.75 (1H, m, NH$\underline{CH}$), 4.46 (2H, q, NCH$_2$), 3.32 (2H, dd, CH$\underline{CH_2}$), 2.83 (2H, dd CH$\underline{CH_2}$), 1.33 (3H, t, NCH$_2$$\underline{CH_3}$); and

ESIMS: M+1: 350.

e) Morpholino 6-(2,3-dihydro-1H-inden-2-yl)amino-1-ethyl-1,4-dihydro-4-oxo-1,5-naphthyridine-3-carboxamide

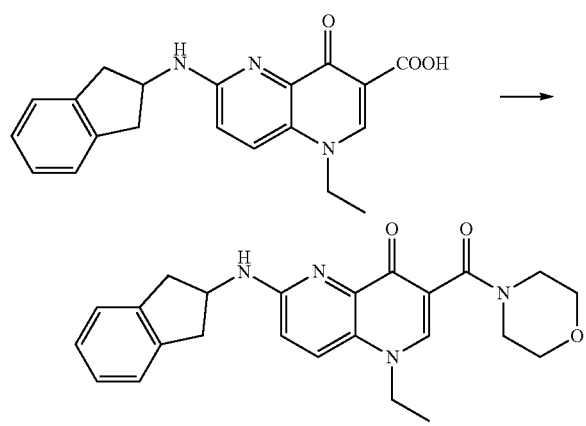

A mixture of 6-(2,3-dihydro-1H-inden-2-yl)amino-1-ethyl-1,4-dihydro-4-oxo-1,5-naphthyridine-3-carboxylic acid (200 mg), HBTU (250 mg) and N,N-diisopropylethylamine (150 mg) in dry DMF (1.5 ml) were stirred for 1 h at RT. Finally morpholine (100 mg) was added and the reaction mixture was stirred overnight. After a standard ethyl acetate/aqueous work-up, the residue from the evaporated organic layer was purified by passing through silica gel column using acetone as a mobile phase to give the 6-(2,3-dihydro-1H-inden-2-ylamino)-1-ethyl-1,4-dihydro-4-oxo-1,5-naphthyridine-3-(~150 mg).

$^1$H NMR (300 MHz, DMSO-$d_6$) δ 8.00 (1H, s, H-2), 7.89 (1H, dd, H-8), 7.30 (1H, d, H-7), 7.22-7.10 (4H, m, Ar), 6.93 (1H, d, NH), 4.75 (1H, m, NH$\underline{CH}$), 4.23 (2H, q, N$\underline{CH_2}$), 3.56-3.27 (8H, bm, morpholino), 3.27 (2H, dd, CH$\underline{CH_2}$), 2.76 (2H, dd CH$\underline{CH_2}$), 1.27 (3H, t, NCH$_2$$\underline{CH_3}$); and

ESIMS: M+1: 419.

Example 3

Preparation of morpholino 6-(2,3-dihydro-1H-inden-2-ylamino)-1-ethyl-1,4-dihydro-4-oxo-1,7-naphthyridine-3-carboxamide (Example 3)

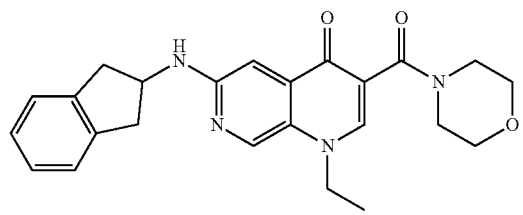 [SMILES: CCn1cc(C(=O)N2CCOCC2)c(=O)c2cc(NC3Cc4ccccc4C3)ncc21]

a) 2,5-Dichloropyridine-4-carboxylic Acid

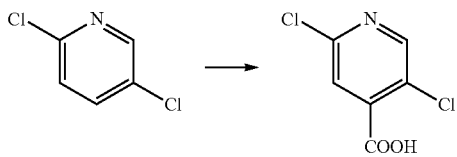 [SMILES: Clc1ccc(Cl)nc1 ; O=C(O)c1cc(Cl)ncc1Cl]

At −75° C., 2,5-dichloropyridine (3.7 g) was added to a solution of butyl lithium (25 ml, 1M) and N,N,N',N'',N''-pentamethyldiethylenetriamine (5.3 ml) in THF (50 ml) under a nitrogen atmosphere at −75° C. and the reaction mixture stirred for 2 h, poured onto dry ice, and water (50 ml) added. The aqueous phase was washed with diethyl ether; acidified to pH 2 and the white solid filtered off dried to give the product (2.5 g), a known compound, for the next reaction, without further characterization other than ascertaining that the compound was one spot by tlc with the expected molecular weight (M−1) of 190.

b) Ethyl 3-(2,5-dichloropyridin-4-yl)-3-oxopropionoate

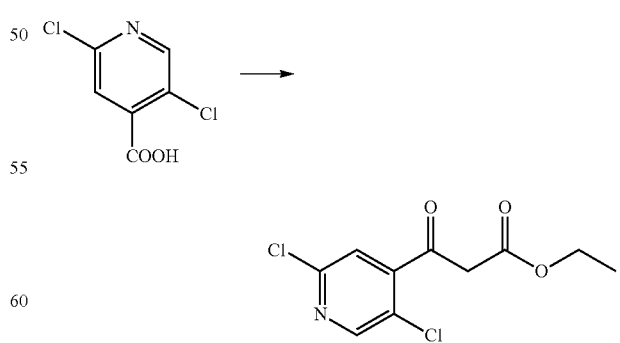

A mixture of 2,5-dichloropyridine-4-carboxylic acid (2 g) and SOCl$_2$ (10 ml) and 1 drop of DMF were heated under reflux for 2 h, and all SOCl$_2$ and DMF removed under reduced pressure to give the crude acid chloride as the remaining residue. Separately, a suspension of potassium ethyl malonate (5 g) in acetonitrile (100 ml) was cooled to 0° C., magnesium chloride (4 g) and triethylamine (4 ml) were added, the ice bath removed and the reaction stirred at RT for 3 h. A solution of the crude acid chloride in DCM (25 ml) was carefully added to the malonate slurry and the resulting mixture stirred at RT overnight. Aqueous HCl (100 ml, 1M) was added and stirring continued for 1 h. This mixture was then extracted with diethyl ether (200 ml×3), the organic layer washed with saturated sodium bicarbonate (200 ml×2) and brine (200 ml), dried over anhydrous magnesium sulfate, filtered and concentrated. The title compound was obtained as light yellow oil (1.6 g) which was on-reacted without further purification and without further characterization other than ascertaining that the compound was one spot by tlc with the expected molecular weight (M−1) of 260.

c) Preparation of 3-(2,5-dichloropyridin-4-yl)-2-(2-ethylamino)-ethylene-1-yl)-3-oxopropanoate

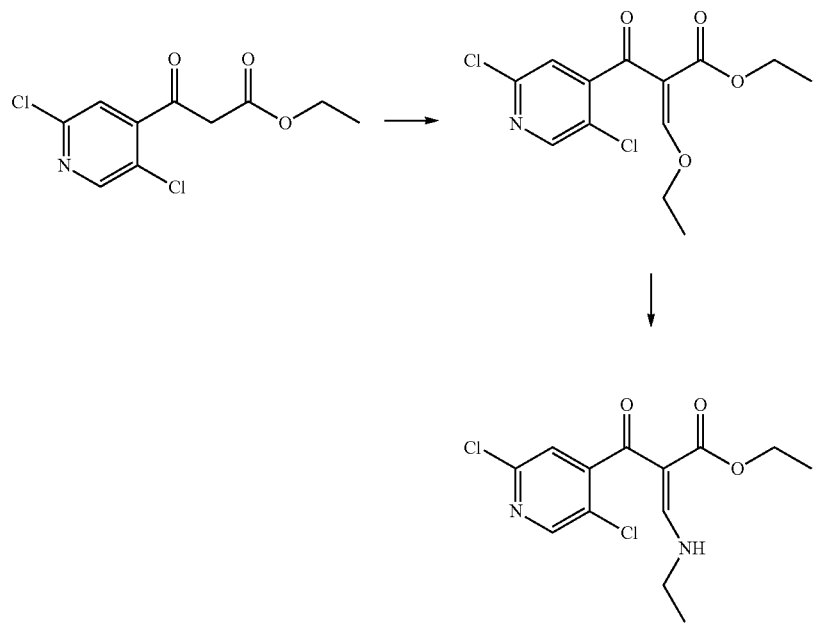

A solution of ethyl 3-(2,5-dichloropyridin-4-yl)-3-oxopropanoate (1.6 g) and triethylorthoformate (1.6 mL) in acetic anhydride (6 ml) was heated at 130° C. for 2 h with stirring. After cooling to RT, all solvent was removed in vacuo, toluene added, removed in vacuo, and this procedure repeated once more. The remaining crude residue was re-dissolved in THF (50 mL) and the ethyl amine (70% in water, 5 ml) was added dropwise with stirring at RT and stirring continued further for 3 h. The reaction mixture was then extracted with DCM (200 ml×3), the organic layer washed with water, dried over magnesium sulfate, filtered, and then all DCM removed under reduced pressure to give the crude product. This crude product was triturated with diethyl ether to give the pure Example 3c as a mixture of E,Z-isomers of the enamine (1.5 g).
ESIMS: m/z 317.0 [M+H]+.

$^1$H NMR (300 MHz, CDCl$_3$): δ 11.05 (bs, 0.8H, NH), 9.75 (bs, 0.2H, NH), 8.34 (s, 1H), 8.24 (s, 0.5H), 8.19 (s, 0.5H), 7.15 (s, 1H), 3.9-4.1 (m, 2H), 3.5-3.6 (m, 2H), 1.41 (t, 3H), 1.03 (t, 3H).

d) Preparation of Ethyl 6-chloro-1-ethyl-1,4-dihydro-4-oxo-1,7-naphthyridine-3-carboxylate

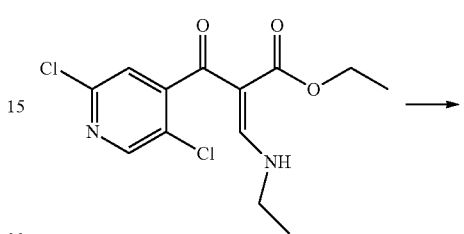

-continued

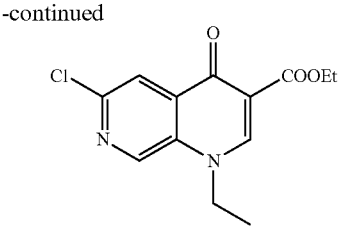

A mixture of 3-(2,5-dichloropyridin-4-yl)-2-(2-ethylamino)-ethylene-1-yl)-3-oxopropanoate (1.2 g) and potassium carbonate (1 g) was heated at 100° C. in DMF (30 ml) for 12 hours. After a standard ethyl acetate/aqueous work-up, the residue from the evaporated organic layer gave the product, ethyl 6-chloro-1-ethyl-1,4-dihydro-4-oxo-1,7-naphthyridine-3-carboxylate (1 g).
ESIMS: m/z 281.0 [M+H]+.

¹H NMR (300 MHz, CDCl₃): δ 8.80 (s, 1H), 8.53 (s, 1H), 8.33 (s, 1H), 4.43 (q, J=6 Hz, 2H), 4.36 (q, J=7 Hz, 2H), 1.63 (t, J=7 Hz, 3H), 1.43 (t, J=6 Hz, 3H).

e) Preparation of Morpholino 6-chloro-1-ethyl-1,4-dihydro-4-oxo-1,7-naphthyridine-3-carboxamide

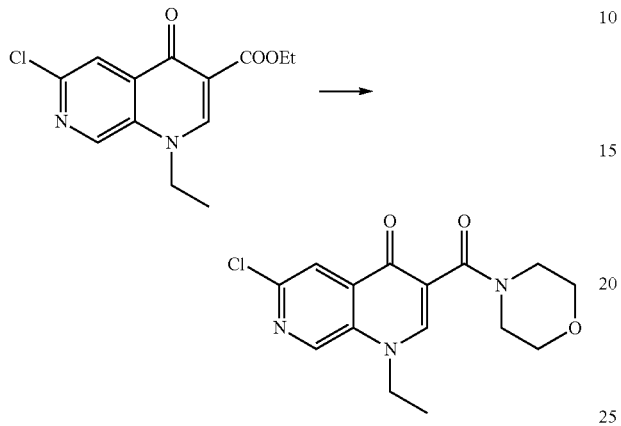

A mixture of trimethylaluminium (4 ml, 2M), morpholine (600 mg) in dry DCM (15 ml) were stirred for 1 h at 35° C. under nitrogen. After 1 h, ethyl 6-chloro-1-ethyl-1,4-dihydro-4-oxo-1,7-naphthyridine-3-carboxylate (900 mg) was added and the reaction mixture stirred o/n at the same temperature. Next day, 1M HCl (10 ml) was added carefully with stirring. After a standard ethyl acetate/aqueous work-up, the residue from the evaporated organic layer gave the morpholino 6-chloro-1-ethyl-1,4-dihydro-4-oxo-1,7-naphthyridine-3-carboxamide (700 mg).

ESIMS: m/z 322.0 [M+H]⁺.

¹H NMR (300 MHz, CDCl₃): δ 8.84 (s, 1H), 8.29 (s, 1H), 8.11 (s, 1H), 4.34 (q, J=7.3 Hz, 2H), 4.22 (m, 1H), 3.3-3.8 (m, 8H), 1.63 (t, J=7.3 Hz, 3H).

f) Preparation of Morpholino 6-(2,3-Dihydro-1H-inden-2-ylamino)-1-ethyl-1,4-dihydro-4-oxo-1,7-naphthyridine-3-carboxamide (Example 3)

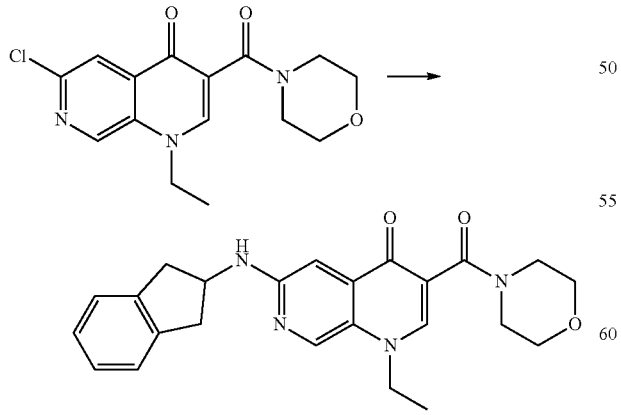

A mixture of 6-chloro-1-ethyl-1,4-dihydro-morpholino-4-oxo-1,7-naphthyridine-3-carboxamide (100 mg) and 2-aminoindane (in excess) was heated at 135° C. for 12 h. The reaction mixture was cooled to RT, ethyl acetate (100 ml) and water (20 ml) was added. The organic phase was separated, concentrated under reduced pressure and subjected to chromatography (SiO₂, 80% ethyl acetate in hexane) gave the product Example 3 (22% yield).

MS: m/z 419.0 [M+H]⁺.

¹H NMR (300 MHz, CDCl₃): δ 8.62 (s, 1H, ArH), 8.01 (s, 1H, ArH), 7.28-7.18 (m, 5H, 5×ArH), 5.57 (bs, 1H, NH), 4.61 (m, 1H, NHCH), 4.27 (q, 2H, CH₂CH₃), 3.80 (m, 6H, morpholino), 3.49 (m, 4H, morpholino+CHCH₂), 2.98 (dd, 2H, CHCH₂), 1.60 (t, 3H, CH₃).

Example 4

Preparation of Methylpiperazino 6-(2,3-dihydro-1H-inden-2-ylamino)-1-ethyl-1,4-dihydro-4-oxo-1,8-naphthyridine-3-carboxamide (Example 4)

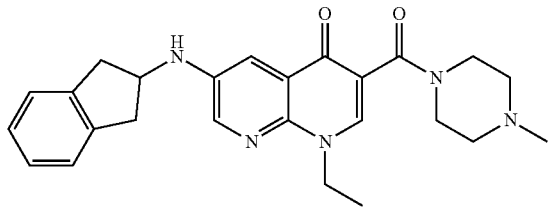 [SMILES: CCn1cc(C(=O)N2CCN(C)CC2)c(=O)c2cc(NC3Cc4ccccc4C3)cnc21]

Trimethylaluminium (1 ml, 2M in toluene) was injected via syringe into a stirred solution of 1-methylpiperazine (100 mg, 1 mmol) in DCM (10 ml). The reaction was stirred at room temperature for 1 h and then treated with ethyl 6-(2,3-dihydro-1H-inden-2-ylamino)-1,4-dihydro-4-oxo-1,5-naphthyridine-3-carboxylate (188.5 mg, 0.5 mmol). The resulting mixture was stirred at room temperature for 16 h and then poured into 5 ml of 2M HCl aq. The organic compound was extracted with ethyl acetate (3×10 ml) and the combined extract was dried over MgSO₄, filtered and concentrated under reduced pressure to afford the crude oil (120 mg crude). Chromatography of a small quantity of the crude gave the desired product (40 mg).

ESIMS: m/z=432.0 [M+H]⁺.

¹H-NMR (300 MHz, CDCl₃): δ 8.15 (d J=2.2, 1H), 8.09 (s, 1H), 7.80 (d, J=2.2 Hz, 1H), 7.15-7.25 (m, 4H), 4.30-4.50 (m, 4H), 3.78 (s, 2H), 3.35-3.50 (m, 4H), 2.86 (dd, 1.1 Hz, 2H), 2.48 (t, J=2 Hz, 4H), 2.30 (s, 3H), 1.47 (t, J=2.4 Hz, 3H).

Example 5

Preparation of Cyclopropylamino 6-(2,3-dihydro-1H-inden-2-ylamino)-1-ethyl-1,4-dihydro-4-oxo-1,8-naphthyridine-3-carboxamide (Example 5)

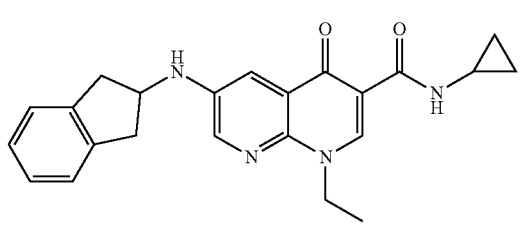 [SMILES: CCn1cc(C(=O)NC2CC2)c(=O)c2cc(NC3Cc4ccccc4C3)cnc21]

Trimethylaluminium (1 ml, 2M in toluene) was injected via syringe into a stirred solution of cyclopropylamine (57 mg, 1 mmol) in DCM (10 ml). The reaction was stirred at room temperature for 1 h and then treated with ethyl 6-(2,3-dihydro-1H-inden-2-ylamino)-1,4-dihydro-4-oxo-1,5-naphthyridine-3-carboxylate (188.5 mg, 0.5 mmol). The resulting mixture was stirred at room temperature for 16 h and then poured into 5 ml of 2M HCl aq. solution. The organic compound was extracted with ethyl acetate (3×10 ml) and the combined extract was dried over MgSO$_4$, filtered and concentrated under reduced pressure to afford the crude oil (150 mg crude). Chromatography of a small quantity of the crude gave the desired product (80 mg).

ESIMS: m/z=389.0 [M+H]$^+$.

$^1$H-NMR (300 MHz, CDCl$_3$): δ 10.01 (s, 1H), 8.81 (s, 1H), 8.18 (s, 1H), 7.80 (s, 1H), 7.15-7.25 (m, 4H), 4.30-4.51 (m, 4H), 3.42 (dd, J=5.0, 5.0 Hz, 2H), 2.88-2.97 (m, 3H), 1.45 (t, J=4.2 Hz, 3H); 0.77-0.82 (m, 2H), 0.60-0.65 (m, 2H).

Example 6

Preparation of Diethylamino 6-(2,3-dihydro-1H-inden-2-ylamino)-1-ethyl-1,4-dihydro-4-oxo-1,8-naphthyridine-3-carboxamide (Example 6)

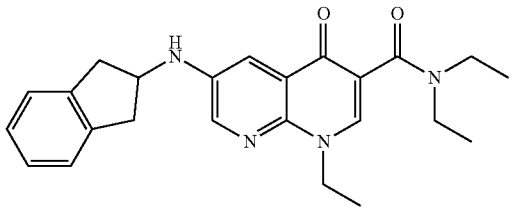 [SMILES: CCN(CC)C(=O)c1cn(CC)c2ncc(NC3Cc4ccccc4C3)cc2c1=O]

Trimethylaluminium (1 ml, 2M in toluene) was injected via syringe into a stirred solution of diethylamine (73 mg, 1 mmol) in DCM (10 ml). The reaction was stirred at room temperature for 1 h and then treated with ethyl 6-(2,3-dihydro-1H-inden-2-ylamino)-1,4-dihydro-4-oxo-1,5-naphthyridine-3-carboxylate (188.5 mg, 0.5 mmol). The resulting mixture was stirred at room temperature for 16 h and then poured into 5 ml of 2M HCl aq. solution. The organic compound was extracted with ethyl acetate (3×10 ml) and the combined extract was dried over MgSO$_4$, filtered and concentrated under reduced pressure to afford the crude oil (135 mg crude). Chromatography of the crude gave the desired product (100 mg)

ESIMS: m/z=405.0 [M+H]$^+$.

$^1$H-NMR (300 MHz, CDCl$_3$): δ 8.15 (d, J=2.2 Hz, 1H), 7.85 (s, 1H), 7.76 (d, J=2.2 Hz, 1H), 7.09-7.25 (m, 4H), 4.56 (d, J=5.6 Hz, 1H), 4.28-4.38 (m, 3H), 3.4-3.52 (m, 2H), 3.32-3.40 (m, 4H), 2.85 (dd, J=11, 3 Hz, 2H), 1.39 (t, J=5.6 Hz, 3H); 1.38 (t, J=5 Hz, 3H), 1.07 (t, J=5 Hz, 3H).

Example 7

Preparation of Ethyl 6-(3,4,5-trimethoxybenzoylamide)-1-ethyl-1,4-dihydro-4-oxo-1,8-naphthyridine-3-carboxylate (Example 7)

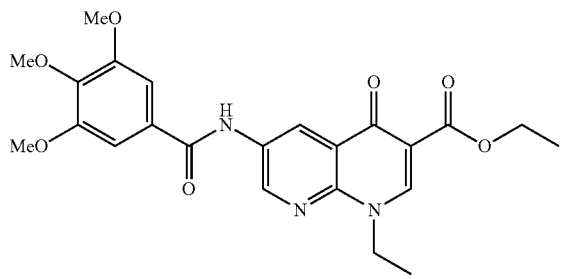 [SMILES: CCOC(=O)c1cn(CC)c2ncc(NC(=O)c3cc(OC)c(OC)c(OC)c3)cc2c1=O]

To the solution of ethyl 1-ethyl-1,4-dihydro-6-amino-4-oxo-1,8-naphthalidine-3-carboxylate (261 mg, 1 mmol) in dichloromethane (5 ml) was treated with 3,4,5-trimethoxybenzoyl chloride (460 mg, 2 mmol) at 5° C. The reaction mixture was then heated to 60° C. for 16 h. The reaction mixture was poured into ice and the product was extracted with ethyl acetate (3×10 ml). The combined extract was dried over MgSO$_4$ and concentrated under reduced pressure to afford the crude product (220 mg). Chromatography of a small quantity of the crude using 10% ethyl acetate in hexane afforded the desired product (30 mg).

ESIMS: m/z=455.9 [M+H]$^+$.

$^1$H-NMR (300 MHz, CDCl$_3$): δ 9.69 (s, 1H), 9.42 (s, 1H), 8.87 (s, 1H), 8.68 (s, 1H), 7.24 (s, 1H), 7.14 (s, 1H), 4.51 (q, J=9, 5 Hz, 2H), 3.88 (s, 9H), 3.38-3.47 (m, 2H), 1.48 (t, J=6 Hz, 3H), 1.18 (t, J=6 Hz, 3H).

Example 8

Preparation of 4-fluorophenylamino 6-(2,3-dihydro-1H-inden-2-ylamino)-1-ethyl-1,4-dihydro-4-oxo-1,8-naphthyridine-3-carboxamide (Example 8)

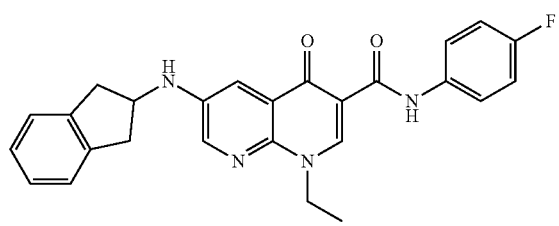 [SMILES: CCn1cc(C(=O)Nc2ccc(F)cc2)c(=O)c2cc(NC3Cc4ccccc4C3)cnc21]

Trimethylaluminium (1 ml, 2M in toluene) was injected via syringe into a stirred solution of 4-fluoroaniline (111 mg, 1 mmol) in DCM (10 ml). The reaction was stirred at room temperature for 1 h and then treated with ethyl 6-(2,3-dihydro-1H-inden-2-ylamino)-1,4-dihydro-4-oxo-1,5-naphthyridine-3-carboxylate (188.5 mg, 0.5 mmol). The resulting mixture was stirred at room temperature for 16 h and then poured into 5 ml of 2M HCl aq. Solution. The organic compound was extracted with ethyl acetate (3×10 ml) and the combined extract was dried over MgSO$_4$, filtered and concentrated under reduced pressure to afford the crude (160 mg). Chromatography of a small quantity of the crude gave the desired product (90 mg).

ESIMS: m/z=443.0 [M+H]$^+$.

$^1$H-NMR (300 MHz, CDCl$_3$): δ 8.86 (s, 1H), 8.20 (d, J=1.8 Hz, 1H), 7.83 (d, J 1.8 Hz, 1H), 7.69-7.74 (m, 2H), 7.16-7.24 (m, 4H), 6.98-7.04 (t, J=7 Hz, 2H), 4.50 (q, J=14, 6 Hz, 2H), 4.44 (s broad, 2H), 3.45 (d, J=14 Hz, 2H), 2.91 (d, J=14 Hz, 2H), 1.46 (t, J=8 Hz, 3H).

Example 9

Preparation of 4-biphenylamino-6-(2,3-dihydro-1H-inden-2-ylamino)-1-ethyl-1,4-dihydro-4-oxo-1,8-naphthyridine-3-carboxamide (Example 9)

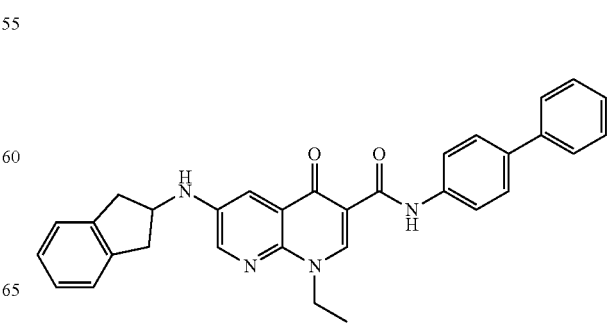

Trimethylaluminium (1 ml, 2M in toluene) was injected via syringe into a stirred solution of 4-aminobiphenyl (169 mg, 1 mmol) in DCM (10 ml). The reaction was stirred at room temperature for 1 h and then treated with ethyl 6-(2,3-dihydro-1H-inden-2-ylamino)-1,4-dihydro-4-oxo-1,5-naphthyridine-3-carboxylate (188.5 mg, 0.5 mmol). The resulting mixture was stirred at room temperature for 16 h and then poured into 5 ml of 2M HCl aq. solution. The organic compound was extracted with ethyl acetate (3×10 ml) and the combined extract was dried over $MgSO_4$, filtered and concentrated under reduced pressure to afford the crude product (140 mg). Chromatography of a small quantity of the crude gave the desired product (50 mg).

ESIMS: m/z=501.0 $[M+H]^+$.

$^1$H-NMR (300 MHz, $CDCl_3$): δ 8.90 (s, 1H), 8.21 (d, J=3.5 Hz, 1H), 7.84-7.88 (m, 3H), 7.57-7.61 (m, 4H), 7.41 (t, J=6.8 Hz, 3H), 7.16-7.32 (m, 5H), 4.52 (q, J=10, 6 Hz, 2H), 4.37-4.44 (m, 2H), 3.46 (dd, J=15, 5 Hz, 2H), 2.92 (dd, J=15, 3 Hz, 2H), 1.52 (t, J=6 Hz, 3H).

Example 10

Preparation of Ethyl 6-(isobutyrylamide)-1-ethyl-1,4-dihydro-4-oxo-1,8-naphthyridine-3-carboxylate (Example 10)

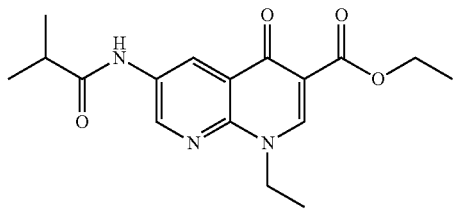 [SMILES: CCOC(=O)c1cn(CC)c2ncc(NC(=O)C(C)C)cc2c1=O]

To the solution of ethyl 1-ethyl-1,4-dihydro-6-imino-4-oxo-1,8-naphthalidine-3-carboxylate (261 mg, 1 mmol) in dichloromethane (5 ml) was treated with isobutyryl chloride (213 mg, 2 mmol) at 5° C. The reaction mixture was then heated to 60° C. for 16 h. The reaction mixture was poured into ice and the product was extracted with ethyl acetate (3×10 ml). The combined extract was dried over $MgSO_4$ and concentrated under reduced pressure to afford the crude product (220 mg). Chromatography of a small quantity of the crude using 10% ethyl acetate in hexane afforded the desired product (NMR data indicates that the product was a mixture of cis and trans-isomers (due to amide linkage).

ESIMS: m/z=332.0 $[M+H]^+$.

$^1$H-NMR (300 MHz, $CDCl_3$): δ 9.74 (s), 9.54 (d, J=2.5 Hz.), 9.3-9.31 (m), 8.85 (s), 8.72 (d, J=2.5 Hz.), 8.66 (s), 8.62 (d, J=2.5 Hz.), 8.59 (s), 4.43-4.53 (m, 2H), 4.28-4.35 (m, 2H), 3.41-3.50 (m, 2H), 2.77-2.86 (m, 1H), 2.60-2.69 (m, 1H), 1.41-1.50 (m), 1.31-1.36 (t), 1.18-1.25 (m).

Biological Data
Screening of the Anxiolytic Effect
Light Dark Test

The light dark paradigm is based on a conflict between the innate aversion of rodents to brightly illuminated areas and on the spontaneous exploratory behaviour of the mice. If given a choice between a large brightly compartment versus a small dark compartment they spontaneously prefer the dark part. Anxiolytic compounds have been found to increase the number of entries into the bright compartment and the total time spent there. Anxiogenic compounds were observed to work in the opposite way.

The apparatus consists of two PVC (polyvinylchloride) boxes (19×19×15 cm) covered with Plexiglas. One of these boxes is darkened. The other box is illuminated by 100 W desk lamp placed 15 cm above and providing an illumination of about 4400 Lux. An opaque plastic tunnel (5×7×10 cm) separates the dark box from the illuminated one.

Animals were placed individually in the lit box, with head directed towards the tunnel. The time spent in the lit box and the number of transitions between the two boxes was recorded over a 5 min period after the first entry of the animal in the dark box. The total walked distance in the lit box was also recorded. Animals scored without entry into the lit box were excluded from the analysis.

Test Compounds and Treatment

The compounds in Table 1 were tested in the light-dark test (indicated in the LD column). +=a significant anxiolytic effect in one of the three parameters measured in the LD model, ++ represents a significant effect in 2 parameters and +++ is significance in all three. The parameters are: time spent in the lit area, number of transitions into the lit area, or total walked distance in the lit area. The minimum effective dose in mg/kg is also shown.

The test compound was prepared in 5% PEG400-0.9% NaCl.

It was administrated orally, 60 minutes before the implementation of the test.

Mean±sem of 10 mice
Elevated Plus Maze

The Elevated Plus Maze (EPM) situation rests on the conflict between the innate tendencies of rodents to explore novel environments and avoid open and brightly lit areas. In this task the mouse is placed in the centre of the maze. From here it can walk down any of four runways. Two of the arms are well lit and open, and the other two are enclosed and dimly lit. Mice prefer the closed arms but will venture out into the open arms. The amount of time spent in the open arms and the number of times the mice enter the open arms are recorded. The total walked distance in the open arms is also recorded. "Anxious" mice will spend little time in the open arms and make very few entries into the open arms.

The apparatus is made of polyvinylchloride materials and consists of four equal exploratory arms (45×10 cm) which are all interconnected by a small platform (10×10 cm). Two arms are open and two others are closed with walls (30 cm high). The apparatus is placed 66 cm above the floor. A videotracking system is used to record the test (ViewPoint, France). The video camera is placed at 2.50 m above the equipment and connected to the computer via a video capture card (Pinnacle Systems, France).

A trial consists of placing an animal on the central platform facing a closed arm. The number of entries and the duration spent in open arms are automatically recorded by a videotrack system during a 5 minute period.

The apparatus is cleaned between each animal using alcohol (70%).

Test Compounds and Treatment

The compounds in Table 1 were tested in the Elevated plus maze (indicated in the EPM column). +=a significant anxiolytic effect in one of the three parameters measured in the LD model, ++ represents a significant effect in 2 parameters and +++ is significance in all three. The parameters are: time spent in the open arms, number of transitions into the open arms, or total walked distance in the open arms. The minimum effective dose in mg/kg is also shown.

The test compound was prepared in 5% PEG400-0.9% NaCl.

It was administered orally, 60 minutes before the implementation of the test.

Mean±sem of 10 rats.

Marble Burying

The Marble Burying test is used as a model for both anxiety and obsessive compulsive disorders. Mice have a natural tendency to bury marbles under the bedding when placed in a cage with rows of evenly spaced marbles on the floor. Suppression of this spontaneous burying has been used as a measure of anxiolytic drug action. Mice pre-treated with benzodiazepines and different classes of antidepressants bury less marbles when compared to the control mice The apparatus consists of transparent polycarbonate cages (30 cm×18 cm×19 cm) containing a 5 cm layer of fine sawdust bedding and 20 glass marbles (diameter: 1.5 cm) spaced evenly along the walls of the cage. Each animal is placed individually in the cage where it remains for a 20 min test session. On termination of the test session the animals are removed from the cage and the number of marbles at least two-thirds buried in the sawdust is recorded.

Test Compounds and Treatment

Example 1 was tested in the Marble Burying model. The minimum effective dose in mg/kg is indicated in the MB column in Table 1.

The test compound was prepared in 5% PEG400-0.9% NaCl.

It was administered orally, 60 minutes before the implementation of the test.

Mean±sem of 10 mice.

Screening of the Sedative or Stimulating Effect of Compounds in the Modified Open Field Open Field The open field (dark) is used to measure the spontaneous motor activity of mice in a quiet, dark environment. This system is useful for discriminating the sedating or stimulating properties of test compounds on spontaneous locomotion and can thus provide a preliminary indication of potentially adverse effects such as sedation.

The apparatus is an open plexiglass cage (52×52 cm) with 40 cm walls. The animal's movements are tracked by a computerised video tracking system, consisting of an overhead camera, diode sensors placed underneath the floor of the cage, computer and video analyser software (ViewPoint, France). The video camera is placed at 2.50 m above the cage and connected to the computer via a video capture card (Pinnacle Systems, France). The video tracking system is set in a way that the floor of the OF is divided into nine equal squares. The total number of crossed squares and the total walked distance are recorded.

Each animal is singly placed in a corner of the apparatus and its locomotor activity is automatically recorded over a period of 20 minutes.

The apparatus is cleaned between each animal with alcohol (70%).

Test Compounds and Treatment

The below items were tested in the Open Field as indicated by an entry in the OF column. NS=no sedation; S=sedation. The maximum non-sedating dose in mg/kg is shown.

Test compound was prepared in 5% PEG400-0.9% NaCl. It was administered orally, 60 minutes before the implementation of the test.

Mean±sem of 10 mice (#N.B. NT means "Not Tested")

TABLE 1

| Example Number | Structure | LD | OF | EPM rat | MB |
|---|---|---|---|---|---|
| 1 | 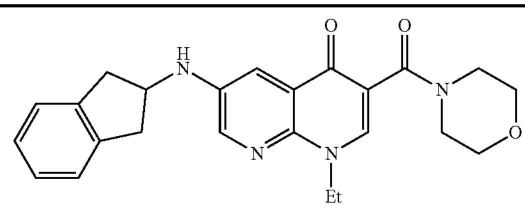 | ++ 0.01 | NS 100 | +++ 0.1 | +++ 1 |
| 2 | 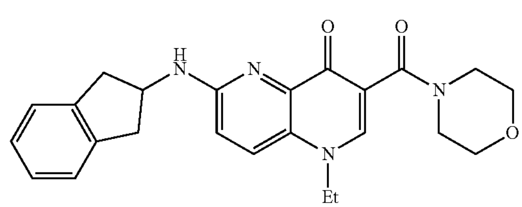 [SMILES: CCn1cc(C(=O)N2CCOCC2)c(=O)c2nc(NC3Cc4ccccc4C3)ccc21] | +++ 30 | S 5 | NT | NT |
| 3 | 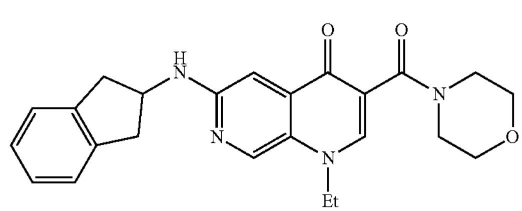 [SMILES: CCn1cc(C(=O)N2CCOCC2)c(=O)c2cc(NC3Cc4ccccc4C3)ncc21] | ++ 10 | NT | NT | NT |

TABLE 1-continued

| Example Number | Structure | LD | OF | EPM rat | MB |
|---|---|---|---|---|---|
| 4* | 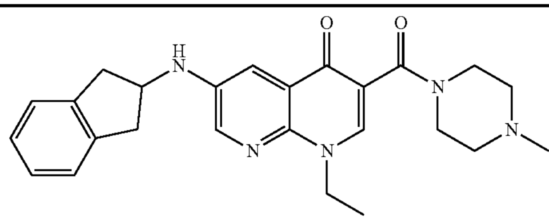 | ++ 20 | NT | NT | NT |
| 5* | 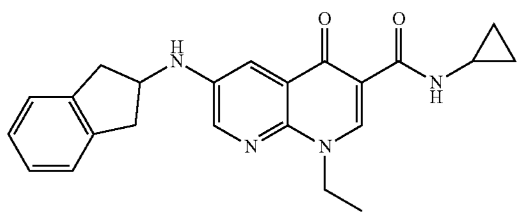 [SMILES: CCn1cc(C(=O)NC2CC2)c(=O)c2cc(NC3Cc4ccccc4C3)cnc21] | + 20 | NT | NT | NT |
| 6* | 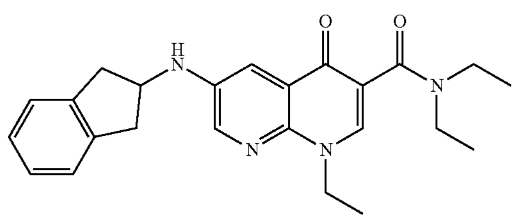 [SMILES: CCN(CC)C(=O)c1cn(CC)c2ncc(NC3Cc4ccccc4C3)cc2c1=O] | ++ 20 | NS 20 | NT | NT |
| 7* | 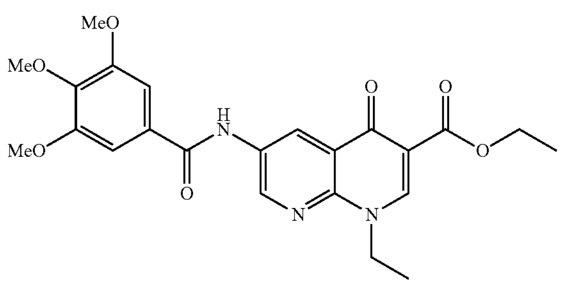 [SMILES: CCOC(=O)c1cn(CC)c2ncc(NC(=O)c3cc(OC)c(OC)c(OC)c3)cc2c1=O] | ++ 20 | S 20 | NT | NT |
| 8* | 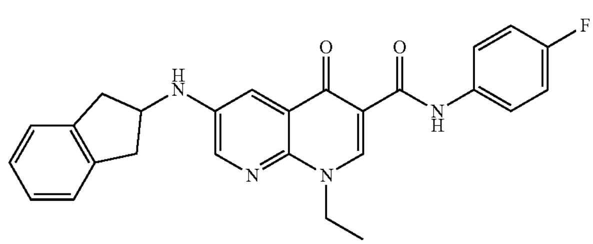 [SMILES: CCn1cc(C(=O)Nc2ccc(F)cc2)c(=O)c2cc(NC3Cc4ccccc4C3)cnc21] | ++ 20 | NS 20 | NT | NT |
| 9* | 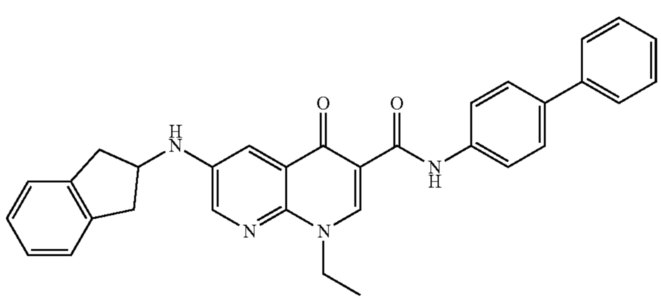 [SMILES: CCn1cc(C(=O)Nc2ccc(-c3ccccc3)cc2)c(=O)c2cc(NC3Cc4ccccc4C3)cnc21] | +++ 20 | NS 20 | NT | NT |

TABLE 1-continued

| Example Number | Structure | LD | OF | EPM rat | MB |
|---|---|---|---|---|---|
| 10* | 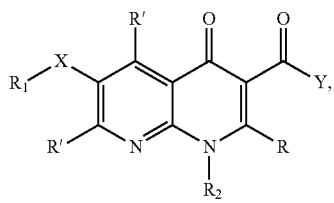 | +++ 20 | NS 20 | NT | NT |

*20 mg/kg is the only dose tested in the LD box and OF.

What is claimed is:

1. A method for treating anxiety associated with autism spectrum disorders (ASD) in children, the method comprising administering to a patient in need thereof a compound of formula (If), or a pharmaceutically acceptable salt thereof:

$$\text{(If)}$$

wherein X represents O or NR″;
R″ is selected from H, optionally substituted alkyl, optionally substituted aryl, optionally substituted cycloalkyl, optionally substituted acyl, optionally substituted alkenyl, optionally substituted heterocyclyl, optionally substituted heteroaryl, optionally substituted oxysulfinyl, optionally substituted oxysulfonyl, optionally substituted sulfinyl, and optionally substituted sulfonyl;
Y represents OR‴ or $NR_3R_4$;
R‴ is H or optionally substituted alkyl;
R represents H or optionally substituted alkyl;
$R_1$ represents optionally substituted cycloalkyl, optionally substituted cycloalkenyl, optionally substituted alkyl, optionally substituted acyl, optionally substituted aryl, optionally substituted heterocyclyl, or optionally substituted heteroaryl;
$R_2$ represents H, optionally substituted cycloalkyl, optionally substituted alkyl, optionally substituted acyl, optionally substituted aryl, optionally substituted alkenyl, optionally substituted heterocyclyl, optionally substituted heteroaryl, optionally substituted oxysulfinyl, optionally substituted oxysulfonyl, optionally substituted sulfinyl, or optionally substituted sulfonyl;
$R_3$ and $R_4$ each independently represent optionally substituted alkyl, or wherein $NR_3R_4$ forms an optionally substituted N-containing heteroaryl or optionally substituted N-containing heterocyclyl; and
each R′ is independently selected from the group consisting of hydrogen, halogen, cyano, nitro, amino, optionally substituted alkyl, optionally substituted acyl, alkoxy, optionally substituted aryl, oxyacyl, acyloxy, optionally substituted arylalkyl, optionally substituted sulfinyl, optionally substituted sulfonyl, oxyacylamino, oxythioacyl, thioacyloxy, optionally substituted sulphinylamino, optionally substituted amino, optionally substituted sulphonylamino, optionally substituted thio, oxysulfinylamino, oxysulfonylamino, optionally substituted alkenyl, and optionally substituted alkynyl.

2. The method according to claim 1, wherein each R′ is hydrogen.

3. The method according to claim 1, wherein X is NR″; and
R″ is selected from H, optionally substituted alkyl, optionally substituted aryl, optionally substituted cycloalkyl, optionally substituted acyl, optionally substituted alkenyl, optionally substituted heterocyclyl, optionally substituted heterocyclyl, optionally substituted heteroaryl, optionally substituted oxysulfinyl, optionally substituted oxysulfonyl, optionally substituted sulfinyl, and optionally substituted sulfonyl.

4. The method according to claim 1, wherein Y is $NR_3R_4$, and $NR_3R_4$ forms an optionally substituted N-containing heteroaryl or optionally substituted N-containing heterocyclyl.

5. The method according to claim 1, wherein $R_1$ is an optionally substituted cycloalkyl or optionally substituted cycloalkenyl.

6. The method according to claim 1, wherein $R_1$ is a benzofused $C_5$-$C_7$ cycloalkyl; wherein the benzene ring may be optionally substituted.

7. The method according to claim 1, wherein the compound of formula (If) is:

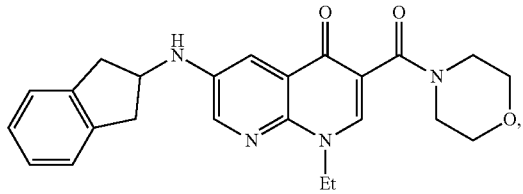 [SMILES: CCn1cc(C(=O)N2CCOCC2)c(=O)c2cc(NC3Cc4ccccc4C3)cnc21]

or a pharmaceutically acceptable salt thereof.

8. The method according to claim 1, wherein the anxiety associated with autism spectrum disorders (ASD) in children is selected from the group consisting of social anxiety disorder, generalized anxiety disorder, separation anxiety disorder, and obsessive compulsive disorder.

9. The method according to claim 7, wherein the anxiety associated with autism spectrum disorders (ASD) in children is selected from the group consisting of social anxiety disorder, generalized anxiety disorder, separation anxiety disorder and obsessive compulsive disorder.

* * * * *